United States Patent
Litzenberger et al.

(10) Patent No.: US 10,034,641 B2
(45) Date of Patent: Jul. 31, 2018

(54) EXTREMITY IMAGING APPARATUS FOR CONE BEAM COMPUTED TOMOGRAPHY

(71) Applicant: Carestream Health, Inc., Rochester, NY (US)

(72) Inventors: Michael A. Litzenberger, Rochester, NY (US); Joseph E. Stagnitto, Rochester, NY (US); Anthony Dirisio, Rochester, NY (US); Peter A. Newman, Pittsford, NY (US); William C. Wendlandt, Rush, NY (US); Douglas M. Csaszar, Webster, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 15/656,364

(22) Filed: Jul. 21, 2017

(65) Prior Publication Data
US 2017/0319151 A1 Nov. 9, 2017

Related U.S. Application Data

(63) Continuation of application No. 14/048,599, filed on Oct. 8, 2013, now Pat. No. 9,717,467.
(Continued)

(51) Int. Cl.
*A61B 6/00* (2006.01)
*A61B 6/03* (2006.01)
*A61B 6/04* (2006.01)

(52) U.S. Cl.
CPC ............ *A61B 6/4291* (2013.01); *A61B 6/032* (2013.01); *A61B 6/035* (2013.01); *A61B 6/04* (2013.01);
(Continued)

(58) Field of Classification Search
CPC ......... A61B 6/025; A61B 6/032; A61B 6/035; A61B 6/04; A61B 6/0492; A61B 6/4085;
(Continued)

(56) References Cited

U.S. PATENT DOCUMENTS

| 4,014,398 A | 3/1977 | Gresko |
| 4,316,091 A | 2/1982 | Bernardi |

(Continued)

FOREIGN PATENT DOCUMENTS

| CN | 1711052 | 11/2003 |
| CN | 1617688 | 5/2005 |

(Continued)

OTHER PUBLICATIONS

International Search Report for International Application No. PCT/US2013/063670 dated Dec. 10, 2013, 3 pages.
(Continued)

*Primary Examiner* — Glen Kao

(57) ABSTRACT

An apparatus for cone beam computed tomography can include a support structure, a scanner assembly coupled to the support structure for controlled movement in at least x, y and z orientations, the scanner assembly can include a DR detector configured to move along at least a portion of a detector path that extends at least partially around a scan volume with a distance D1 that is sufficiently long to allow the scan volume to be positioned within the detector path; a radiation source configured to move along at least a portion of a source path outside the detector path, the source path having a distance D2 greater than the distance D1, the distance D2 being sufficiently long to allow adequate radiation exposure of the scan volume for an image capture by the detector; and a first gap in the detector path.

16 Claims, 40 Drawing Sheets

Related U.S. Application Data

(60) Provisional application No. 61/710,832, filed on Oct. 8, 2012.

(52) U.S. Cl.
CPC .......... *A61B 6/4405* (2013.01); *A61B 6/4429* (2013.01); *A61B 6/4441* (2013.01); *A61B 6/4447* (2013.01); *A61B 6/4452* (2013.01); *A61B 6/467* (2013.01); *A61B 6/50* (2013.01)

(58) Field of Classification Search
CPC ... A61B 6/4233; A61B 6/4405; A61B 6/4429; A61B 6/4441; A61B 6/4447; A61B 6/4452; A61B 6/4482; A61B 6/461; A61B 6/467; A61B 6/50; A61B 6/527; A61B 6/4291
See application file for complete search history.

(56) References Cited

U.S. PATENT DOCUMENTS

| | | | |
|---|---|---|---|
| 4,741,015 | A | 4/1988 | Charrier |
| 5,014,293 | A | 5/1991 | Boyd et al. |
| 5,748,704 | A | 5/1998 | Mazess et al. |
| 6,131,690 | A | 10/2000 | Galando et al. |
| 6,236,704 | B1 | 5/2001 | Navab et al. |
| 6,580,777 | B1 | 6/2003 | Ueki et al. |
| 6,842,502 | B2 | 1/2005 | Jaffray et al. |
| 6,940,941 | B2 | 9/2005 | Gregerson et al. |
| 7,001,045 | B2 | 2/2006 | Gregerson et al. |
| 7,108,421 | B2 | 9/2006 | Gregerson et al. |
| 7,224,764 | B2 | 5/2007 | Sukovic et al. |
| 7,388,894 | B2 | 6/2008 | Sukovic et al. |
| 7,388,941 | B2 | 6/2008 | Sukovic et al. |
| 7,394,888 | B2 | 7/2008 | Sukovic et al. |
| 7,460,636 | B2 | 12/2008 | Ein-Gal |
| 7,471,765 | B2 | 12/2008 | Jaffray et al. |
| 7,558,367 | B1 | 7/2009 | Tinwala et al. |
| 8,210,745 | B2 | 7/2012 | Yorkston et al. |
| 8,348,506 | B2 | 1/2013 | Yorkston et al. |
| 8,746,972 | B2 | 6/2014 | Yorkston et al. |
| 9,240,045 | B2 | 1/2016 | Noshi et al. |
| 9,277,899 | B2 | 3/2016 | Yorkston et al. |
| 2003/0026464 | A1 | 2/2003 | Kamiyama et al. |
| 2003/0072416 | A1 | 4/2003 | Rasche et al. |
| 2004/0022350 | A1 | 2/2004 | Gregerson et al. |
| 2004/0096035 | A1 | 5/2004 | Yamazaki et al. |
| 2004/0120467 | A1 | 6/2004 | Wollenweber |
| 2005/0053185 | A1 | 3/2005 | Sukovic et al. |
| 2005/0053186 | A1 | 3/2005 | Sukovic et al. |
| 2006/0245539 | A1 | 11/2006 | Sukovic et al. |
| 2007/0036274 | A1 | 2/2007 | Haras et al. |
| 2008/0013691 | A1 | 1/2008 | Gregerson |
| 2008/0022890 | A1 | 1/2008 | Doumaux et al. |
| 2008/0037701 | A1 | 2/2008 | Banks |
| 2008/0056440 | A1 | 3/2008 | Fischer et al. |
| 2008/0101533 | A1 | 5/2008 | Ein-Gal |
| 2008/0112534 | A1* | 5/2008 | Defreitas ............ A61B 6/0414 378/37 |
| 2008/0205584 | A1 | 8/2008 | Sukovic et al. |
| 2008/0245972 | A1 | 10/2008 | Drapeau |
| 2008/0285724 | A1 | 11/2008 | Dehler |
| 2009/0080604 | A1 | 3/2009 | Shores et al. |
| 2009/0128351 | A1 | 5/2009 | Ma |
| 2009/0252290 | A1 | 10/2009 | Plut et al. |
| 2010/0278300 | A1* | 11/2010 | Yorkston ............ A61B 6/032 378/20 |
| 2010/0329534 | A1 | 12/2010 | Biermann et al. |
| 2011/0082348 | A1 | 4/2011 | Herold et al. |
| 2011/0210261 | A1 | 9/2011 | Maurer, Jr. |
| 2011/0228901 | A1 | 9/2011 | Yorkston et al. |
| 2011/0280364 | A1 | 11/2011 | Maschke |
| 2012/0043475 | A1 | 2/2012 | Ahn |
| 2012/0059239 | A1 | 3/2012 | Yamaguchi |
| 2012/0078568 | A1 | 3/2012 | Koelling et al. |
| 2012/0256099 | A1 | 10/2012 | Gregerson et al. |
| 2012/0289821 | A1 | 11/2012 | Graumann et al. |
| 2013/0004042 | A1 | 1/2013 | Yang et al. |
| 2013/0032413 | A1 | 2/2013 | Smith et al. |
| 2014/0003583 | A1 | 1/2014 | Krupica et al. |
| 2015/0173703 | A1 | 6/2015 | Siewerdsen et al. |

FOREIGN PATENT DOCUMENTS

| | | |
|---|---|---|
| CN | 101589957 | 5/2009 |
| CN | 102421368 | 5/2010 |
| CN | 202027591 | 4/2011 |
| CN | 102429672 | 9/2011 |
| DE | 198 46 980 | 10/1999 |
| DE | 101 46 915 B4 | 9/2001 |
| DE | 101 47 157 | 4/2003 |
| DE | 10 2005 013 832 | 8/2006 |
| DE | 10 2008 019 646 | 10/2009 |
| EP | 0 119 660 | 9/1984 |
| EP | 1016375 | 12/1999 |
| EP | 0 676 911 | 9/2000 |
| EP | 0 919 187 | 1/2005 |
| EP | 2127696 | 3/2009 |
| JP | 02-228946 | 9/1990 |
| JP | 05-192342 | 8/1993 |
| JP | 07-023942 | 1/1995 |
| JP | H10-328173 | 12/1998 |
| JP | 2001-29342 | 2/2001 |
| JP | 2001-269332 | 10/2001 |
| JP | 2003-088523 | 3/2003 |
| JP | 2005-517486 | 6/2005 |
| JP | 2006-314605 | 11/2006 |
| JP | 2007159598 | 6/2007 |
| JP | 2010-154992 | 7/2010 |
| JP | 2010-200929 | 9/2010 |
| JP | 2013-066784 | 4/2013 |
| WO | 95/21570 | 8/1995 |
| WO | 95/22241 | 8/1995 |
| WO | 95/31936 | 11/1995 |
| WO | 03/070101 | 8/2003 |
| WO | 03/077763 | 9/2003 |
| WO | 2006/042211 | 4/2006 |
| WO | 2006/042211 A2 | 4/2006 |
| WO | 2006/119420 A1 | 11/2006 |
| WO | 2010/078481 | 7/2010 |
| WO | 2011/126555 | 10/2011 |
| WO | 2011/156526 | 12/2011 |

OTHER PUBLICATIONS

International Search Report for International Application No. PCT/US2013/063673 dated Feb. 14, 2014, 4 pages.
International Search Report for International Application No. PCT/US2013/063666 dated Feb. 7, 2014, 3 pages.
International Search Report for International Application No. PCT/US2013/063662 dated Feb. 17, 2014, 3 pages.
Definitions-Merriam-Webster.com. Merriam-Webster, n.d. Wed. Aug. 2, 2016.
European Search Report, Application No. EP 16 19 5074, dated Feb. 1, 2017, 2 pages.
International Search Report for International application No. PCT/US2010/001308, dated Nov. 22, 2010, 2 pages.
International Search Report for International applicatipn No. PCT/US2011/000596, dated Nov. 23, 2011, 2 pages.
Supplementary European Search Report for application No. EP 10 77 2373, dated Apr. 10, 2013, 2 pages.
Page from website=www.planmed.com, 1 page, Mar. 2011.

* cited by examiner

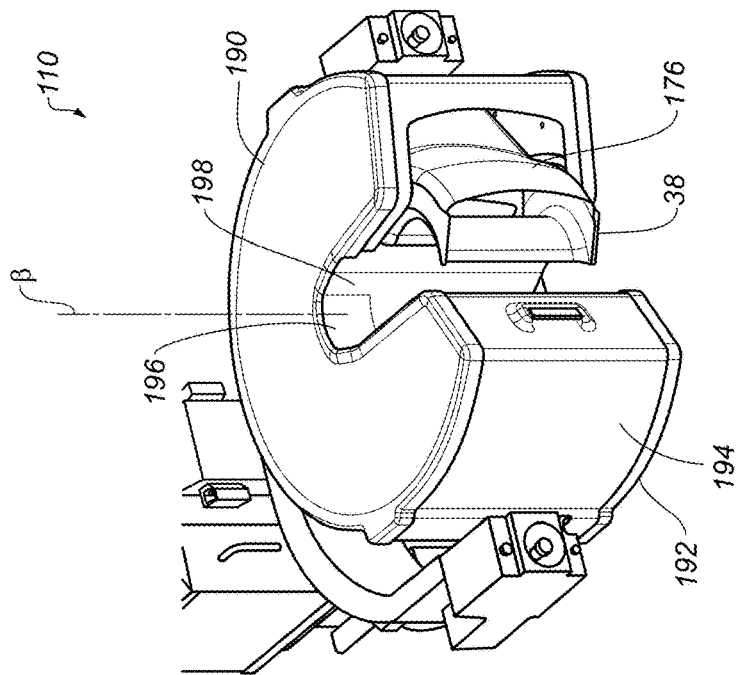
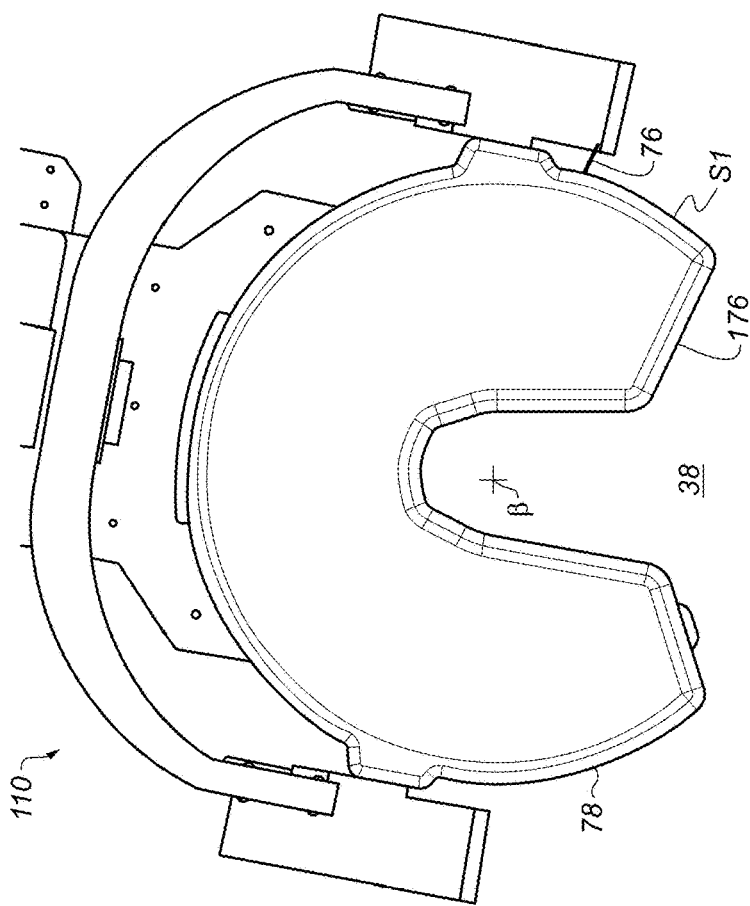
FIG. 16B
FIG. 16A

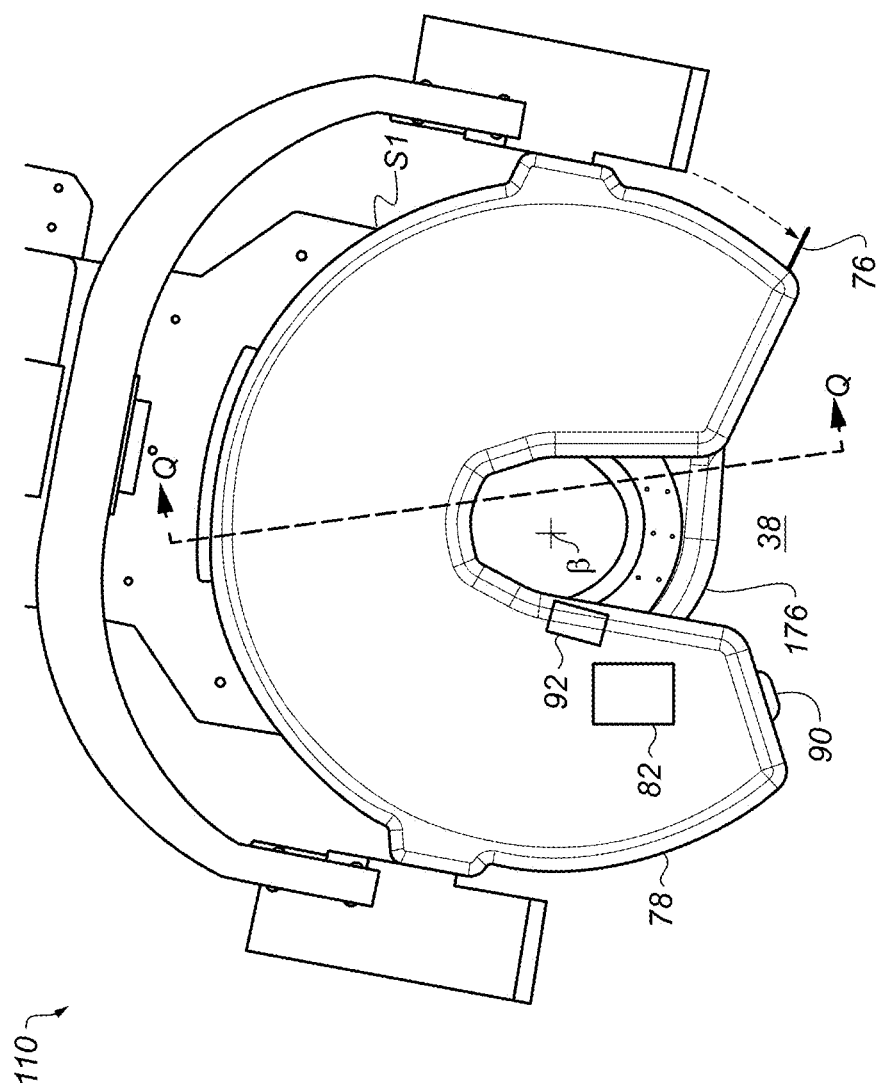

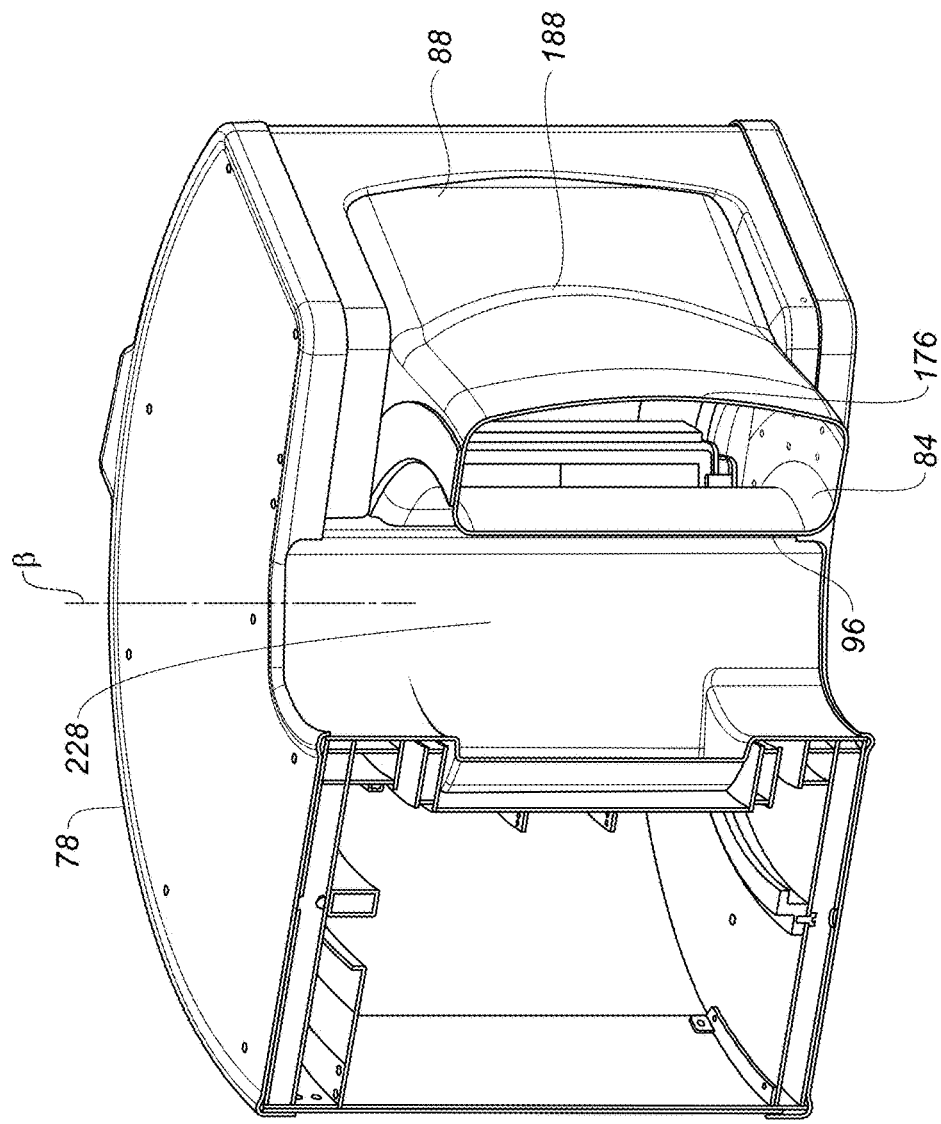

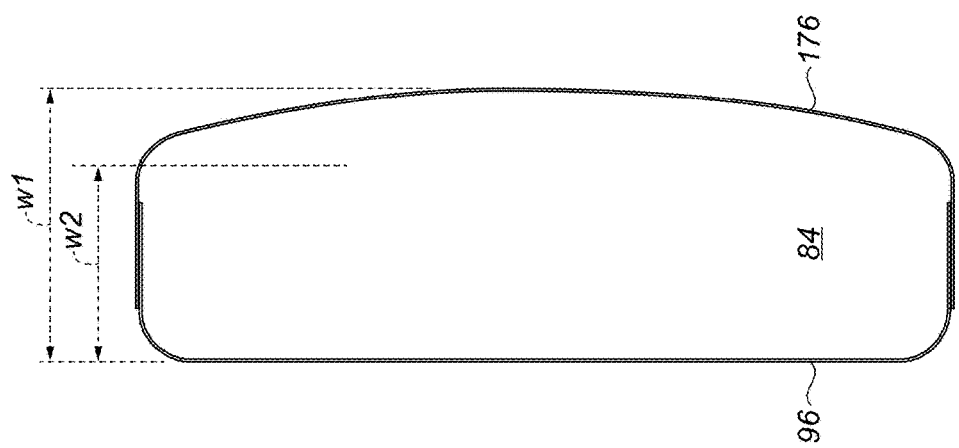

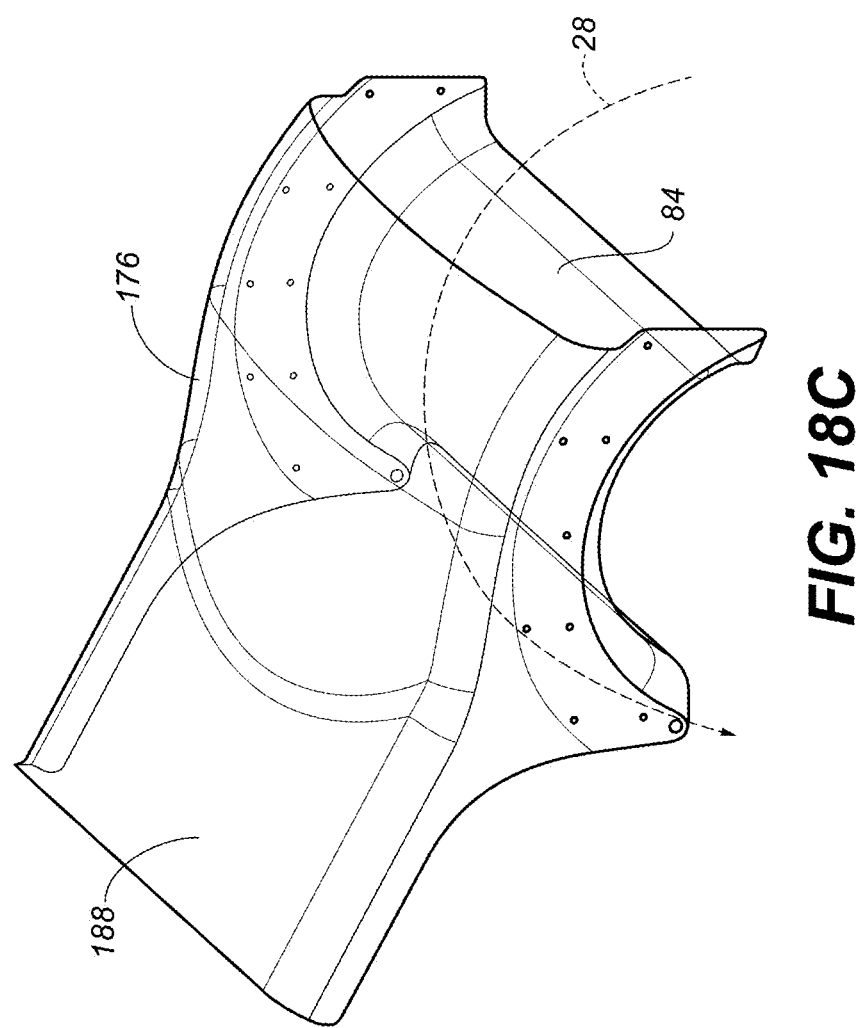

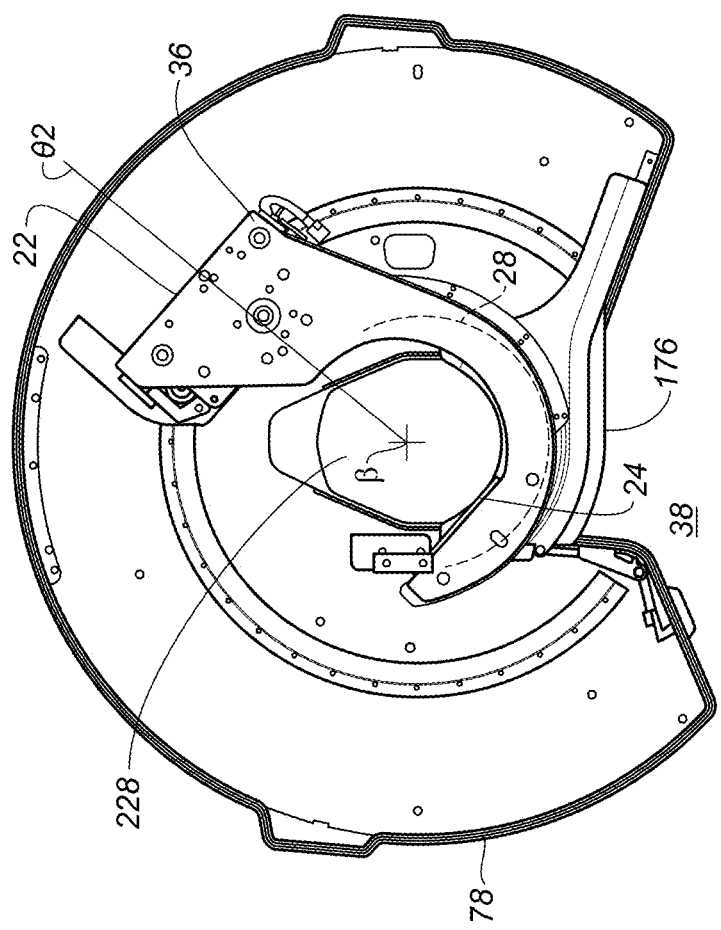

EXTREMITY IMAGING APPARATUS FOR CONE BEAM COMPUTED TOMOGRAPHY

CROSS REFERENCE TO RELATED APPLICATIONS

This application is a continuation of U.S. patent application Ser. No. 14/048,599, filed Oct. 8, 2013, in the name of Litzenberger, et al., entitled EXTREMITY IMAGING APPARATUS FOR CONE BEAM COMPUTED TOMOGRAPHY, which claims the benefit of U.S. Provisional application U.S. Ser. No. 61/710,832, provisionally filed on Oct. 8, 2012, entitled "EXTREMITY SCANNER AND METHODS FOR USING THE SAME", in the names of John Yorkston et al., which is hereby incorporated herein by reference in its entirety.

FIELD OF THE INVENTION

The invention relates generally to diagnostic imaging and in particular to cone beam imaging systems used for obtaining volume images of extremities.

BACKGROUND OF THE INVENTION

3-D volume imaging has proved to be a valuable diagnostic tool that offers significant advantages over earlier 2-D radiographic imaging techniques for evaluating the condition of internal structures and organs. 3-D imaging of a patient or other subject has been made possible by a number of advancements, including the development of high-speed imaging detectors, such as digital radiography (DR) detectors that enable multiple images to be taken in rapid succession.

Cone beam computed tomography (CBCT) or cone beam CT technology offers considerable promise as one type of diagnostic tool for providing 3-D volume images. Cone beam CT systems capture volumetric data sets by using a high frame rate digital radiography (DR) detector and an x-ray source, typically affixed to a gantry that rotates about the object to be imaged, directing, from various points along its orbit around the subject, a divergent cone beam of x-rays toward the subject. The CBCT system captures projections throughout the rotation, for example, one 2-D projection image at every degree of rotation. The projections are then reconstructed into a 3D volume image using various techniques. Among well known methods for reconstructing the 3-D volume image from the 2-D image data are filtered back projection approaches.

Although 3-D images of diagnostic quality can be generated using CBCT systems and technology, a number of technical challenges remain. In some cases, for example, there can be a limited range of angular rotation of the x-ray source and detector with respect to the subject. CBCT Imaging of legs, arms, and other extremities can be hampered by physical obstruction from a paired extremity. This is an obstacle that is encountered in obtaining CBCT image projections for the human leg or knee, for example. Not all imaging positions around the knee are accessible; the patient's own anatomy often prevents the radiation source and image detector from being positioned over a portion of the scan circumference.

To illustrate the problem faced in CBCT imaging of the knee, the top view of FIG. 1 shows the circular scan paths for a radiation source 22 and detector 24 when imaging the right knee R of a patient as a subject 20. Various positions of radiation source 22 and detector 24 are shown in dashed line form. Source 22, placed at some distance from the knee, can be positioned at different points over an arc of about 200 degrees; with any larger arc the paired extremity, left knee L, blocks the way. Detector 24, smaller than source 22 and typically placed very near subject 20, can be positioned between the patient's right and left knees and is thus capable of positioning over the full circular orbit.

A full 360 degree orbit of the source and detector is not needed for conventional CBCT imaging; instead, sufficient information for image reconstruction can be obtained with an orbital scan range that just exceeds 180 degrees by the angle of the cone beam itself, for example. However, in some cases it can be difficult to obtain much more than about 180 degree revolution for imaging the knee or other joints and other applications. Moreover, there can be diagnostic situations in which obtaining projection images over a certain range of angles has advantages, but patient anatomy blocks the source, detector, or both from imaging over that range. Some of the proposed solutions for obtaining images of extremities under these conditions require the patient to assume a position that is awkward or uncomfortable. The position of the extremity, as imaged, is not representative of how the limb or other extremity serves the patient in movement or under weight-bearing conditions. It can be helpful, for example, to examine the condition of a knee or ankle joint under the normal weight load exerted on that joint by the patient as well as in a relaxed position. But, if the patient is required to assume a position that is not usually encountered in typical movement or posture, there may be excessive strain, or insufficient strain, or poorly directed strain or tension, on the joint. The knee or ankle joint, under some artificially applied load and at an angle not taken when standing, may not behave exactly as it does when bearing the patient's weight in a standing position. Images of extremities under these conditions may fail to accurately represent how an extremity or joint is used and may not provide sufficient information for assessment and treatment planning.

Still other difficulties with conventional solutions for extremity imaging relate to poor image quality. For image quality, the CBCT sequence requires that the detector be positioned close to the subject and that the source of the cone beam radiation be at a sufficient distance from the subject. This provides the best image and reduces image truncation and consequent lost data. Positioning the subject midway between the detector and the source, as some conventional systems have done, not only noticeably compromises image quality, but also places the patient too near the radiation source, so that radiation levels are considerably higher.

CBCT imaging represents a number of challenges that also affect other types of volume imaging that employ a radiation source and detector orbiting an extremity over a range of angles. There are various tomographic imaging modes that can be used to obtain depth information for a scanned extremity.

In summary, for extremity imaging, particularly for imaging the lower paired extremities, a number of improvements are needed, including the following:
  (i) improved placement of the radiation source and detector relative to the imaged subject to provide acceptable radiation levels and image quality throughout the scanning sequence, with the capability for at least coarse automated setup for examining an extremity under favorable conditions;
  (ii) system flexibility for imaging at different heights with respect to the rotational axis of the source and detector, including the flexibility to allow imaging with the patient standing or seated comfortably, such as with a foot in an elevated position, for example;

(iii) capability to adjust the angle of the rotational axis to suit patient positioning requirements;

(iv) improved patient accessibility, so that the patient does not need to contort, twist, or unduly stress limbs or joints that may have been injured in order to provide images of those body parts;

(v) improved ergonomics for obtaining the CBCT image, allowing the patient to stand or sit with normal posture, for example. This would also allow load-bearing extremities, such as legs, knees, and ankles, to be imaged under the normal load exerted by the patient's weight, rather than under simulated loading conditions and provide options for supporting the patient; and (vi) adaptability for multi-use imaging, allowing a single imaging apparatus to be configurable for imaging any of a number of extremities, including knee, ankle, toe, hand, elbow, and other extremities. This also includes the capability to operate the imaging system in different imaging modes, including CBCT, two-dimensional (2-D) projection radiography, fluoroscopy, and other tomography modes.

In summary, the capability for straightforward configuration and positioning of the imaging apparatus allows the advantages of CBCT imaging to be adaptable for use with a range of extremities, to obtain volume images under a suitable imaging modality, with the image extremity presented at a suitable orientation under both load-bearing and non-load-bearing conditions, and with the patient appropriately standing or seated.

SUMMARY OF THE INVENTION

An aspect of this application is to advance the art of medical digital radiography.

Another aspect of this application is to address, in whole or in part, at least the foregoing and other deficiencies in the related art.

It is another aspect of this application to provide, in whole or in part, at least the advantages described herein.

It is another aspect of this application to advance the art of diagnostic imaging of extremity body parts, particularly jointed or load-bearing, paired extremities such as knees, legs, ankles, fingers, hands, wrists, elbows, arms, and shoulders.

It is another aspect of this application to provide apparatus and/or method embodiments that adapt to imaging conditions suitable for a range of extremities and/or allows the patient to be in a number of positions for suitable imaging of the extremity.

It is another aspect of this application to provide apparatus and/or method embodiments that increase patient room outside of a scan volume of a CBCT imaging apparatus for placement of at least one part of a patient that si not being imaged. In some embodiments, scanner housings can be shaped to provide additional patient positioning options or clearance.

It is another aspect of this application to provide apparatus and/or method embodiments that provide a door to close a peripheral gap in a scanner that has a shape or cross-sectional shape to increase room within a scan volume.

It is another aspect of this application to provide apparatus and/or method embodiments that provide a handle for a door to close a peripheral gap in a scanner that is positioned outside the peripheral gap.

It is another aspect of this application to provide apparatus and/or method embodiments that provide a detachable grid capability relative to an installed digital radiography detector of a CBCT imaging apparatus.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 16A is a top view of the imaging scanner showing the door open position.

FIG. 16B is a perspective view of the imaging scanner showing a door closing position.

FIG. 16C is a top view of the imaging scanner showing the door closed position.

FIG. 18A is a cutaway view that shows the door in position within the scanner.

FIG. 18B is an outline view of the door showing width tapering.

FIG. 18C is an outline view of the door showing the detector path through the hollow passage of the door.

FIGS. 19A, 19B, 19C, and 19D are top views that show the sequence of movement of scanning components that is allowable when the door of the scanner is closed.

DESCRIPTION OF EXEMPLARY EMBODIMENTS

Figure 2:
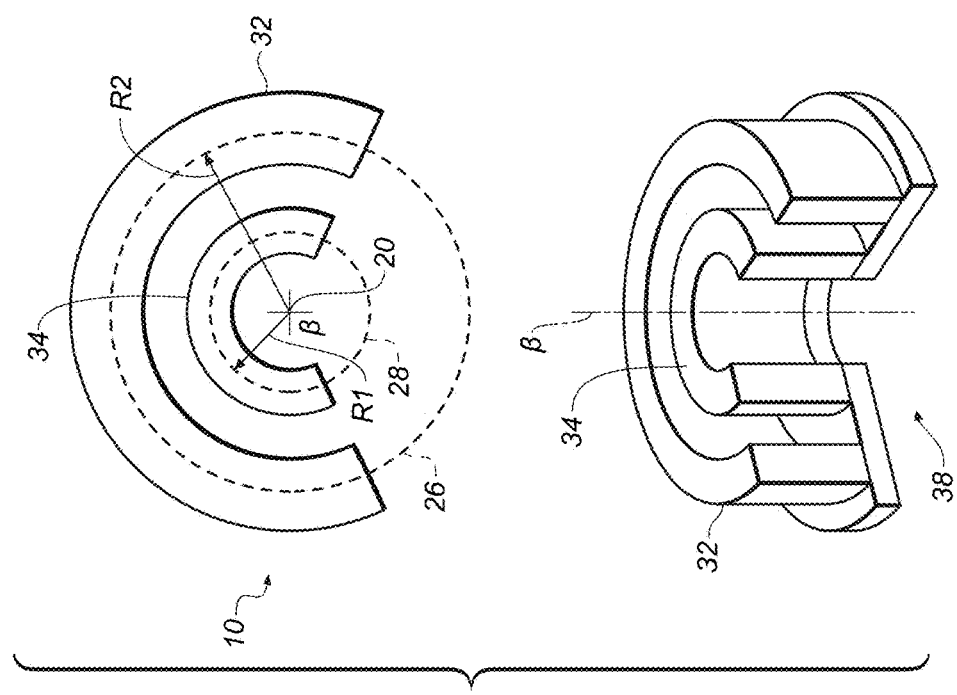
FIG. 2 shows a top and perspective view of the scanning pattern for an imaging apparatus according to an embodiment of the application.
Figure 1:
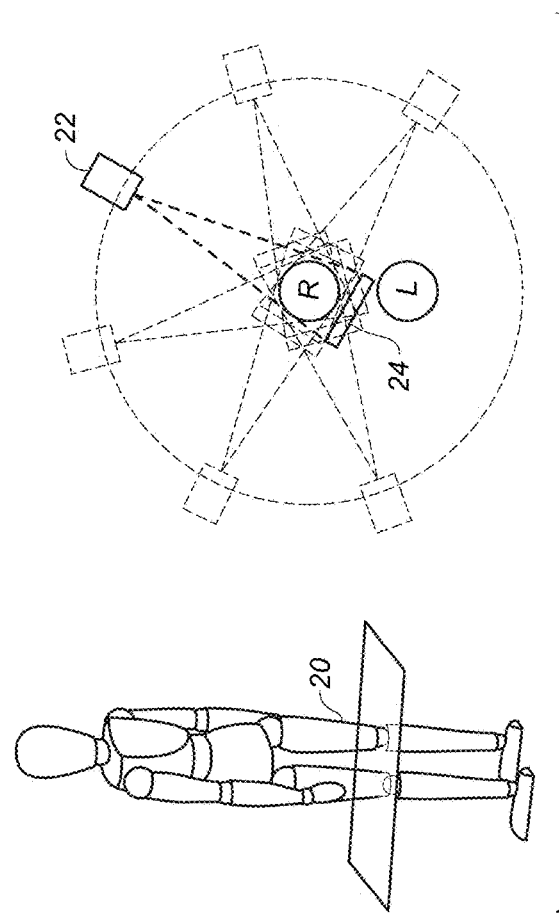
FIG. 1 is a schematic view showing the geometry and limitations of CBCT scanning for portions of the lower leg.

The following is a description of exemplary embodiments of the invention, examples of which are illustrated in the accompanying drawings. Wherever possible, the same reference numbers will be used throughout the drawings to refer to the same or like parts.

For illustrative purposes, principles of the invention are described herein by referring mainly to exemplary embodiments thereof. However, one of ordinary skill in the art would readily recognize that the same principles are equally applicable to, and can be implemented in, all types of radiographic imaging arrays, various types of radiographic imaging apparatus and/or methods for using the same and that any such variations do not depart from the true spirit and scope of the application. Moreover, in the following description, references are made to the accompanying figures, which illustrate specific exemplary embodiments. Electrical, mechanical, logical and structural changes can be made to the embodiments without departing from the spirit and scope of the invention.

In the context of the application, the term "extremity" has its meaning as conventionally understood in diagnostic imaging parlance, referring to knees, legs, ankles, fingers, hands, wrists, elbows, arms, and shoulders and any other anatomical extremity. The term "subject" is used to describe the extremity of the patient that is imaged, such as the "subject leg", for example. The term "paired extremity" is used in general to refer to any anatomical extremity wherein normally two or more are present on the same patient. In the context of the application, the paired extremity is not imaged unless necessary; only the subject extremity is imaged. In one embodiment, a paired extremity is not imaged to reduce patient dose.

A number of the examples given herein for extemporary embodiments of the application focus on imaging of the load-bearing lower extremities of the human anatomy, such as the leg, the knee, the ankle, and the foot, for example. However, these examples are considered to be illustrative and non-limiting.

In the context of the application, the term "arc" or, alternately, or arcuate has a meaning of a portion of a curve, spline or non-linear path, for example as being a portion of a curve of less than 360 degrees or, considered alternately, of less than $2\pi$ radians for a given radius or distance from a central bore.

The term "actuable" has its conventional meaning, relating to a device or component that is capable of effecting an action in response to a stimulus, such as in response to an electrical signal, for example.

As used herein, the term "energizable" relates to a device or set of components that perform an indicated function upon receiving power and, optionally, upon receiving an enabling signal.

In the context of the application, two elements are considered to be substantially orthogonal if their angular orientations differ from each other by 90 degrees, +/−no more than about 10 degrees.

It is instructive to observe that the mathematical definition of a cylinder includes not only the familiar "can-shaped" right circular cylinder, but also any number of other shapes. The outer surface of a cylinder is generated by moving a first straight line element along a closed curve or other path along a base plane, while maintaining the first straight line element parallel to a second, fixed straight line that extends out from the base plane, wherein the moving first straight line intersects a fixed closed curve or base in the base plane. A cube, for example, is considered to have a cylindrical shape according to this definition. A can-shaped cylinder of revolution, for example, is generated when the moving first straight line intersects a circle in the base plane at a right angle. An object is considered to be substantially cylindrical when its overall surface shape is approximated by a cylinder shape according to this definition, with allowance for standard edge rounding, protruding or recessed mechanical and electrical fasteners, and external mounting features.

Certain exemplary embodiments according to the application address the difficulties of extremity imaging by providing an imaging apparatus that defines coordinated non-linear source and detector paths (e.g., orbital, curved, concentric about a center point), wherein components that provide the source and detector paths are configured to allow patient access prior to and following imaging and configured to allow the patient to sit or stand with normal posture during the CBCT image capture series. Certain exemplary embodiments provide this capability by using a detector transport device that has a circumferential access opening allowing positioning of the extremity, wherein the detector transport device is revolved about the positioned extremity once it is in place, enclosing (e.g., partially, substantially, fully) the extremity as it is revolved through at least a portion of the scan.

It is instructive to consider dimensional attributes of the human frame that can be considerations for design of CBCT equipment for scanning extremities. For example, an adult human patient of average height in a comfortable standing position has left and right knees generally anywhere from about 10 to about 35 cm apart. For an adult of average height, exceeding about 35-40 cm (14-15.7 inches) between the knees becomes increasing less comfortable and out of the range of normal standing posture. It is instructive to note that this constraint makes it impractical to use conventional gantry solutions for obtaining the needed 2-D image sequence. For certain exemplary embodiments, either the source or the detector must be able to pass between the legs of a standing patient for knee CBCT imaging, a capability not available with gantry or other conventional solutions.

The perspective and corresponding top views of FIG. 2 show how the scanning pattern is provided for components of CBCT imaging apparatus 10 according to an embodiment of the application. A detector path 28 of a suitable radius R1 from a central axis β is provided for a detector device by a detector transport 34. A source path 26 of a second, larger radius R2 is provided for a radiation source by a source transport 32. In one embodiment, a non-linear source path 26 is greater in length than a non-linear detector path 24. According to an embodiment of the application, described in more detail subsequently, the same transport system provides both detector transport 34 and source transport 32. The extremity, subject 20, is preferably substantially centered along central axis β so that central axis β can be considered as a line through points in subject 20. In one embodiment, an imaging bore or the CBCT apparatus can include or encompass the central axis β. The limiting geometry for image capture is due to the arc of source transport 32, blocked by gap 38 (e.g., for patient anatomy, such as by a paired limb), and thus limited typically to less than about 220 degrees, as noted previously. The circumferential gap or opening 38 can occupy the space between the endpoints of the arc of source path 26. Gap or opening 38 gives space for the patient a place to stand, for example, while one leg is being imaged.

Figure 3C:
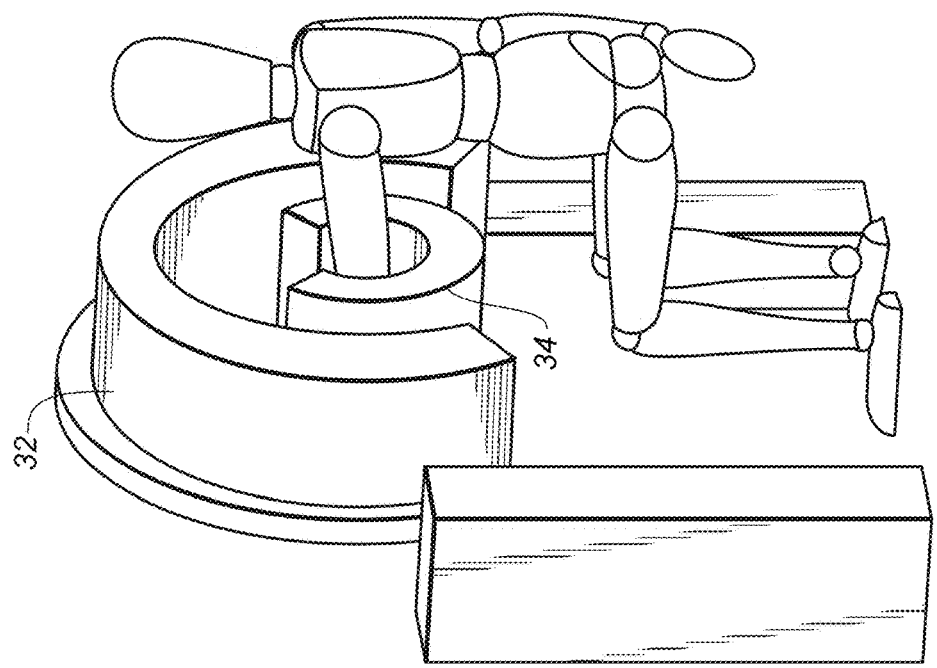
FIG. 3C is a perspective view showing patient access to another imaging apparatus according to an embodiment of the application.
Figure 3A:
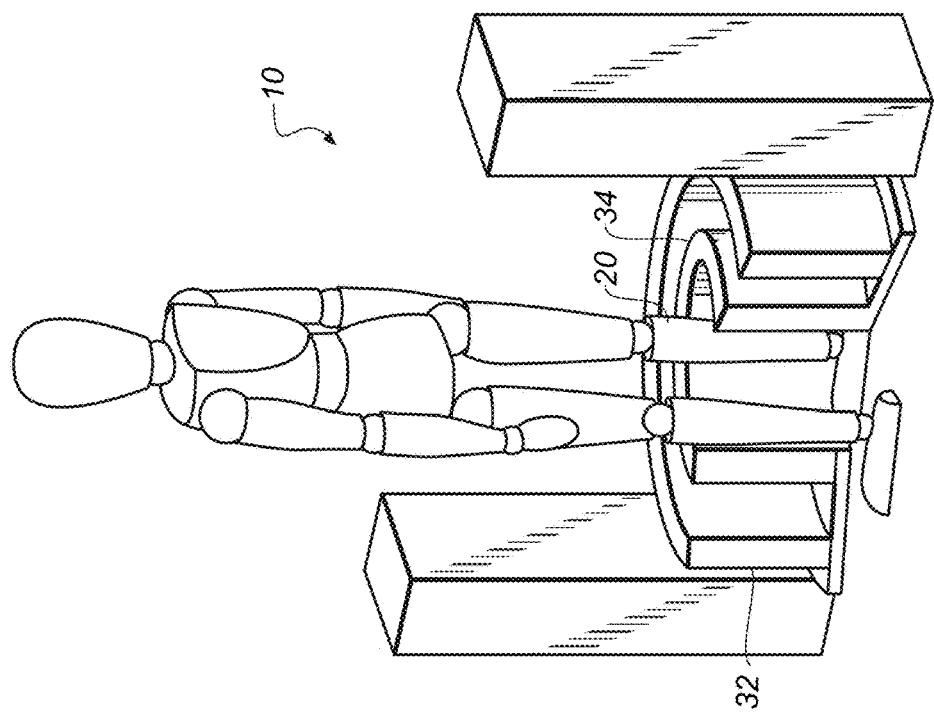
FIG. 3A is a perspective view showing patient access to an imaging apparatus according to an embodiment of the application.
Figure 3B:
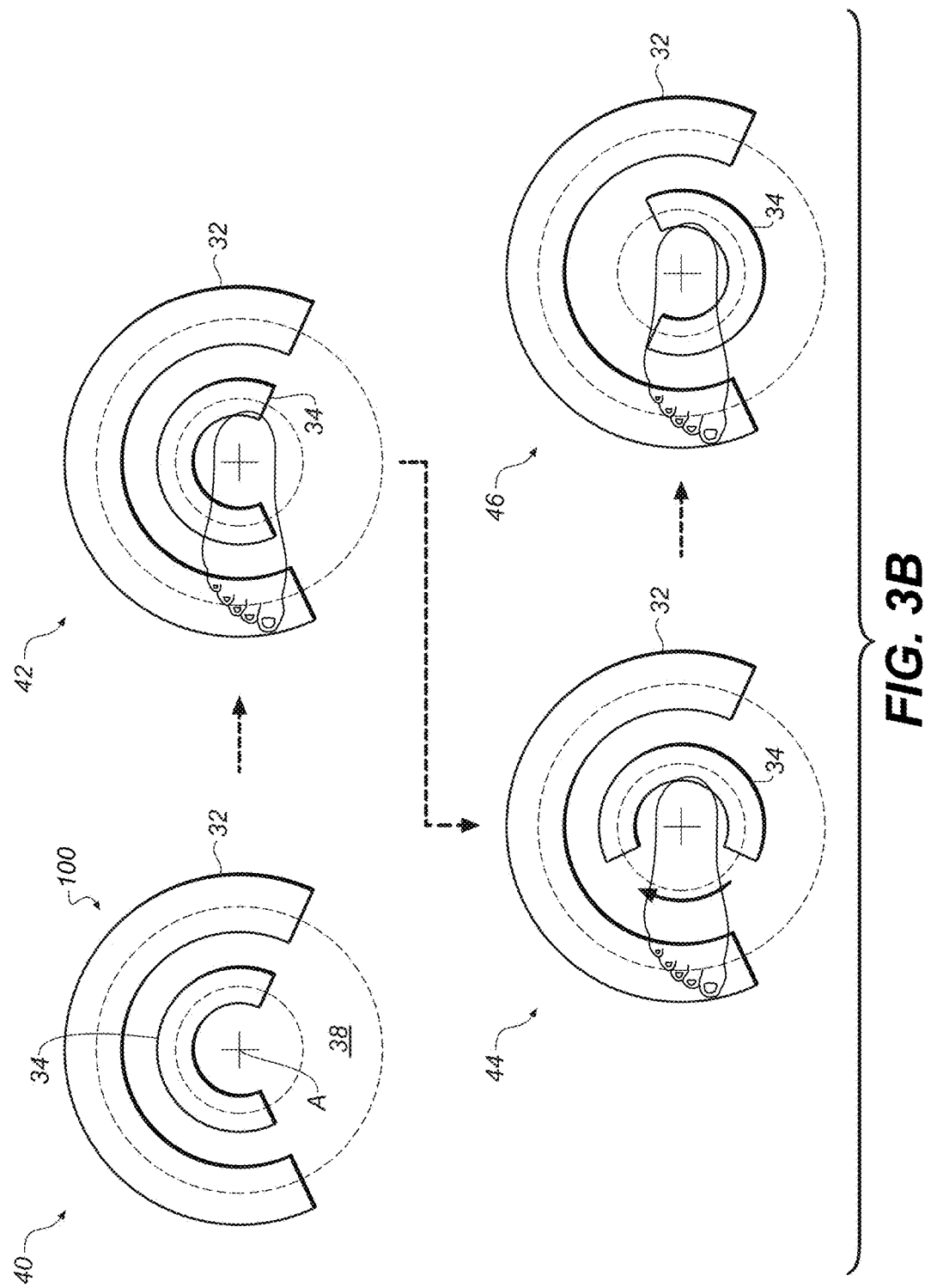
FIG. 3B is a top view showing a sequence of steps for enclosing the extremity to be imaged within the path of the detector transport.

Detector path 28 can extend through circumferential gap 38 to allow scanning, since the detector is not necessarily blocked by patient anatomy but can have a travel path at least partially around an imaged extremity that can extend between the standing patient's legs. Embodiments of the present invention allow temporary restriction of the detector path 28 to allow access for the patient as part of initial patient positioning. The perspective view in FIG. 2, for example, shows detector transport 34 rotated to open up circumferential gap 38 so that it extends from the axis β (e.g., beyond a source path or housing). With detector transport 34 translated to the open position shown in FIG. 3A, the patient can freely move in and out of position for imaging. When the patient is properly in position, detector transport 34 is revolved about axis β by more than 180 degrees; according to an embodiment of the application, detector transport 34 is revolved about axis β by substantially 200 degrees. This patient access and subsequent adjustment of detector transport 34 is shown in successive stages in FIG. 3B. This orbital movement confines the extremity to be imaged more effectively and places detector 24, not visible in FIGS. 2-3B due to the detector transport 34 housing, in position near subject 20 for obtaining the first projection image in sequence. In one embodiment, a detector transport 34 can include shielding or a door over part of the detector path, and/or the gap 38.

Circumferential gap or opening 38 not only allows access for positioning of the subject leg or other extremity, but also allows sufficient space for the patient to stand in normal posture during imaging, placing the subject leg for imaging in the central position along axis β (FIG. 2) and the non-imaged paired leg within the space defined by circumferential gap 38. Circumferential gap or opening 38 extends approximately 180 degrees minus the fan angle (e.g., between ends of the source path), which is determined by source-detector geometry and distance. Circumferential gap or opening 38 permits access of the extremity so that it can be centered in position along central axis β. Once the patient's leg or other extremity is in place, detector transport 34, or a hooded cover or hollow door or other member that defines this transport path, can be revolved into position, closing the detector portion of circumferential gap or opening 38.

Figure 4:
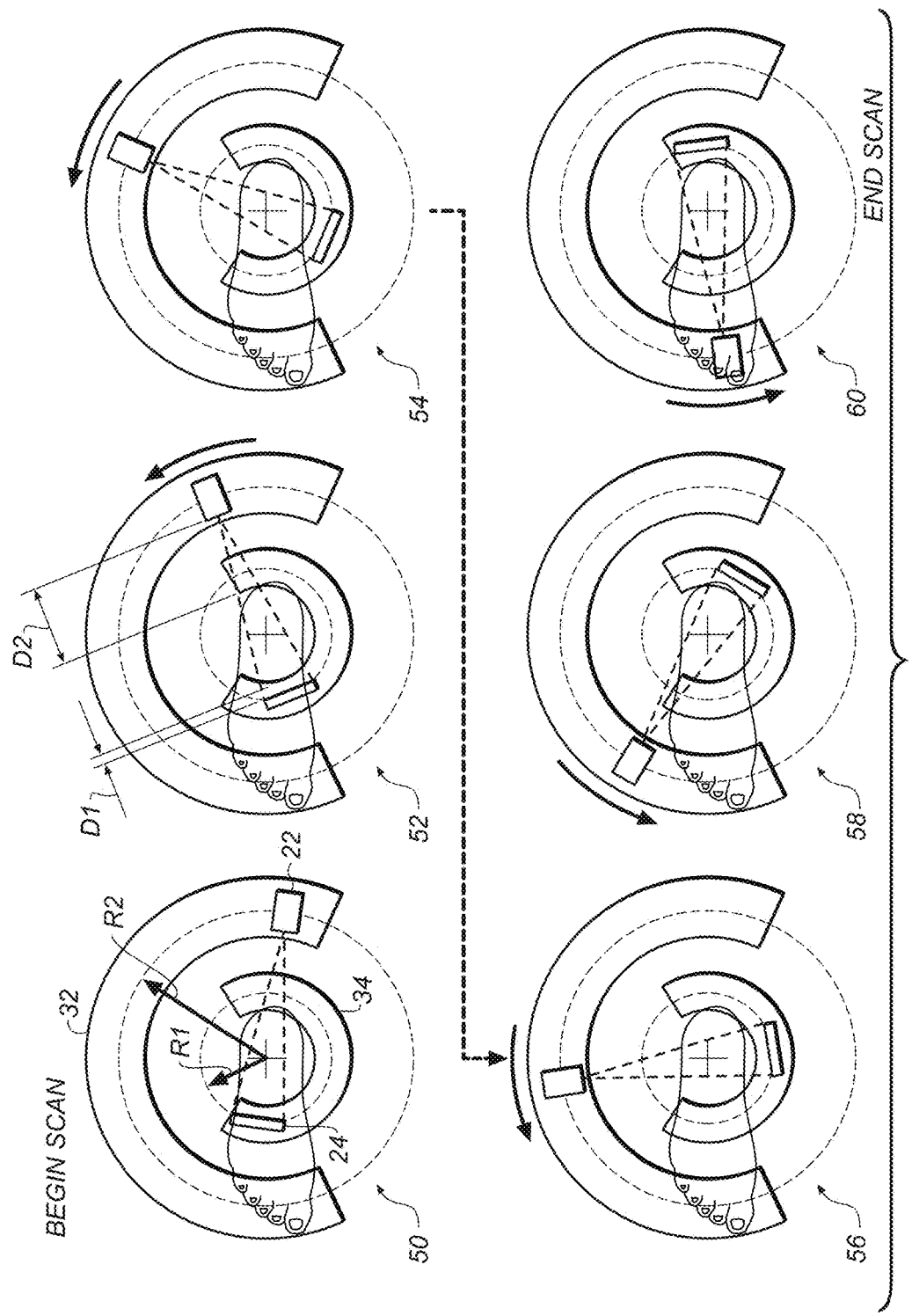
FIG. 4 show portions of the operational sequence for obtaining CBCT projections of a portion of a patient's leg at a number of angular positions when using the imaging apparatus according to an embodiment of the application.

By way of example, the top views of FIG. 4 show portions of the operational sequence for obtaining CBCT projections of a portion of a patient's leg at a number of angular positions when using a CBCT imaging apparatus. The relative positions of radiation source 22 and detector 24, which may be concealed under a hood or chassis, as noted earlier, are shown in FIG. 4. The source 22 and detector 24 can be aligned so the radiation source 22 can direct radiation toward the detector 24 (e.g., diametrically opposite) at each position during the CBCT scan and projection imaging. The sequence begins at a begin scan position 50, with radiation source 22 and detector 24 at initial positions to obtain an image at a first angle. Then, both radiation source 22 and detector 24 revolve about axis β as represented in interim scan positions 52, 54, 56, and 58. Imaging terminates at an end scan position 60. As this sequence shows, source 22 and detector 24 are in opposing positions relative to subject 20 at each imaging angle. Throughout the scanning cycle, detector 24 is within a short distance D1 of subject 20. Source 22 is positioned beyond a longer distance D2 of subject 20. The positioning of source 22 and detector 24 components on each path can be carried out by separate actuators, one for each transport path, or by a single rotatable member, as described in more detail subsequently. It should be noted that scanning motion in the opposite direction, that is, clockwise with respect to the example shown in FIG. 4, is also possible, with the corresponding changes in initial and terminal scan positions.

Figure 5:
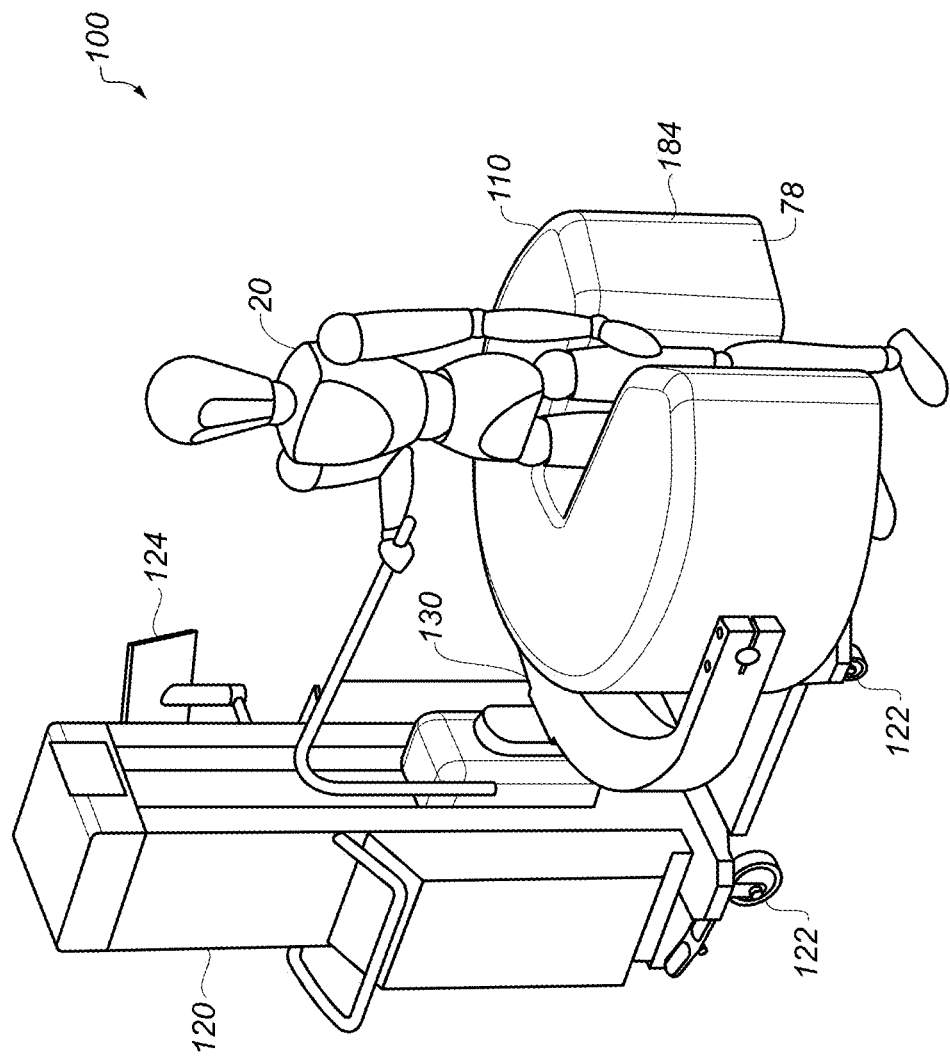
FIG. 5 is a perspective view that shows a CBCT imaging apparatus for extremity imaging according to an embodiment of the application.
Figure 6B:
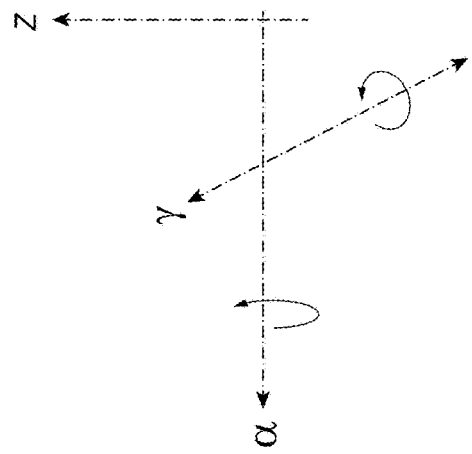
FIG. 6B shows reference axes for rotation and translation.
Figure 6A:
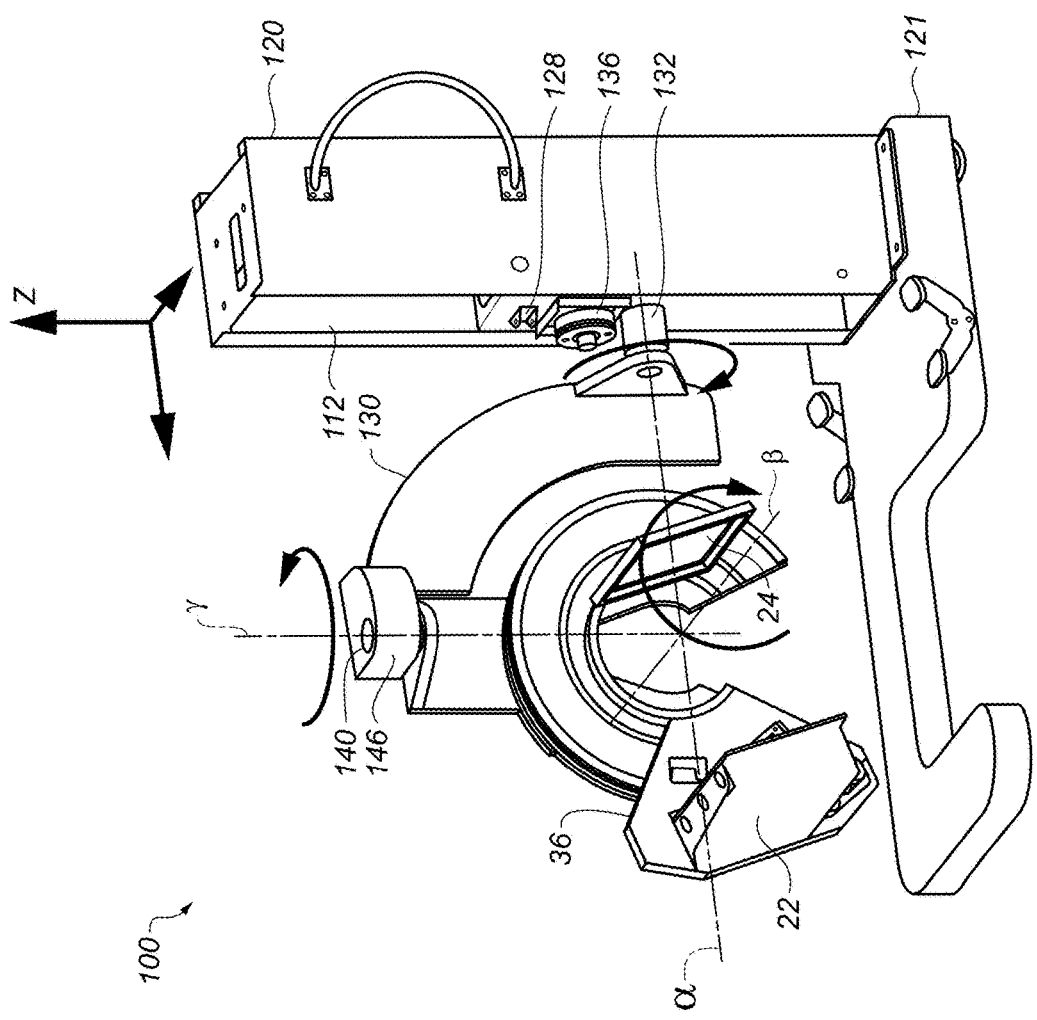
FIG. 6A shows internal components used for imaging ring translation and positioning.

Given this basic operation sequence in which the source 22 and detector 24 orbit the extremity, the usefulness of an imaging system that is adaptable for imaging patient extremities with the patient sitting or standing and in load-bearing or non load-bearing postures can be appreciated. The perspective view of FIG. 5 shows a CBCT imaging apparatus 100 for extremity imaging according to an embodiment of the application. Imaging apparatus 100 has a gimballed imaging ring or scanner 110 that houses and conceals source 22 and detector 24 within a housing 78. FIG. 5 shows their supporting transport mechanisms. Scanner 110 is adjustable in height and rotatable in gimbaled fashion about non-parallel axes, such as about substantially orthogonal axes as described in subsequent figures, to adapt to various patient postures and extremity imaging conditions. A support column 120 supports scanner 110 on a yoke, or bifurcated or forked support arm 130, a rigid supporting element that has adjustable height and further provides rotation of scanner 110 as described subsequently. Support column 120 can be fixed in position, such as mounted to a floor, wall, or ceiling. According to portable CBCT embodiments such as shown in FIG. 6A and elsewhere, support column 120 mounts to a support base 121 that also includes optional wheels or casters 122 for transporting and maneuvering imaging apparatus 100 into position. A control panel 124 can provide an operator interface, such as a display monitor, for entering instructions for apparatus 100 adjustment and operation. In one embodiment, the control panel 124 can include a processor or computer (e.g., hardware, firmware and/or software) to control operations of the CBCT system 100. Support column 120 can be of fixed height or may have telescoping operation, such as for improved visibility when apparatus 100 is moved.

Vertical and Rotational Movement

FIG. 6A shows portions of exemplary internal imaging and positioning mechanisms (with covers removed) for scanner 110 that allow imaging apparatus 100 the capability for imaging extremities with a variety of configurations. FIG. 6B shows rotation axes definitions for scanner 110 positioning. The α-axis and the γ-axis are non-parallel, to allow gimbaled action. According to an embodiment of the application as shown in FIG. 6A, the α-axis and the γ-axis are mutually orthogonal. The α-axis is substantially orthogonal to the z-axis. The intersection of the α-axis and the γ-axis can be offset from support column 120 by some non-zero distance.

First considering the z-axis, FIG. 6A shows an exemplary embodiment to achieve vertical motion. Within support column 120, a vertical carriage translation element 128 is actuated in order to travel upwards or downwards along column 120 within a track 112 in a vertical direction. Carriage translation element 128 has a support shaft 132 that is coupled to an actuator 136 for providing α-axis rotation to forked or C-shaped support arm 130. Forked support arm 130, shown only partially in FIG. 6A to allow a better view of underlying components, is coupled to support shaft 132. X-ray source 22 and receiver 24 are mounted on a rotatable gantry 36 for rotation about a scan or central axis, designated as the β axis. Axis β is orthogonal to the α-axis and the γ-axis.

Figure 6C:
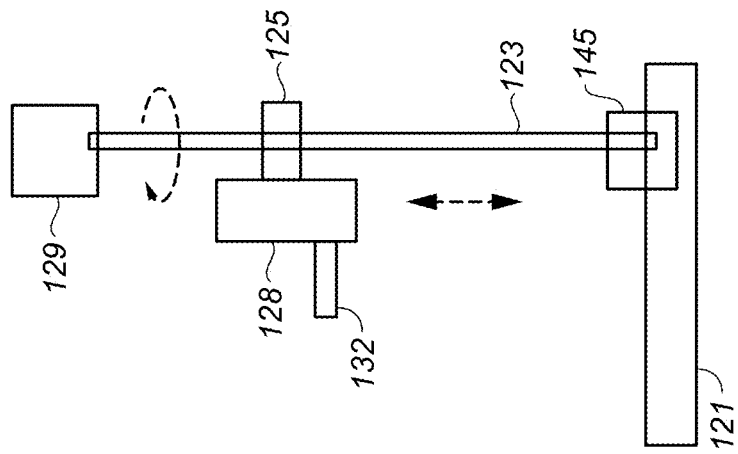
FIG. 6C is a schematic diagram that shows components of the positioning system for the imaging scanner.
Figure 6D:
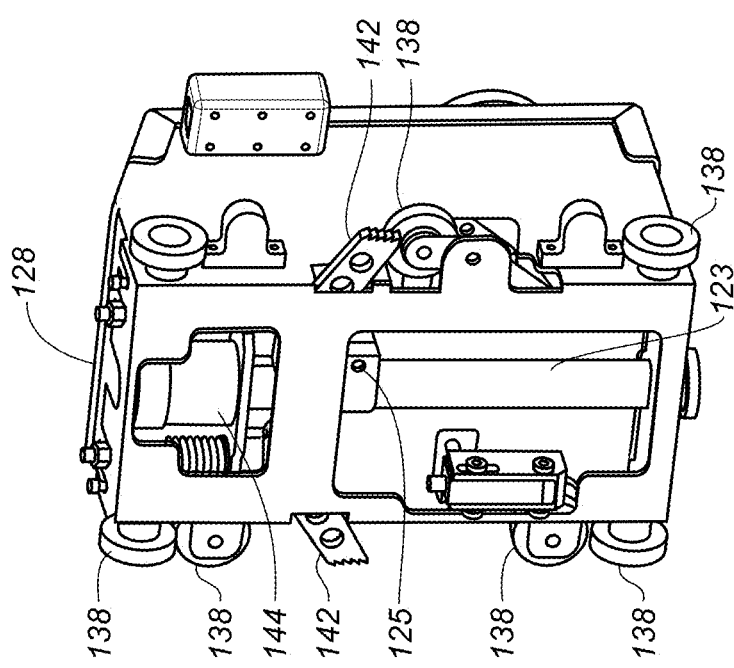
FIG. 6D is a perspective view showing some of the components of a vertical translation apparatus.

It can be appreciated that z-axis translation can be effected in a number of ways. Challenges that must be addressed by the type of system that is used include handling the weight of forked support arm 130 and the imaging scanner 110 that arm 130 supports. This can easily weigh a few hundred pounds. In addition, precautions must be provided for handling conditions such as power loss, contact with the patient, or mechanical problems that hamper positioning movement or operation. According to an embodiment of the application, as shown schematically in FIG. 6C and in the perspective view of FIG. 6D, a vertical actuator 129 rotates a threaded shaft 123. Vertical carriage translation element 128 employs a ball screw mount apparatus 125 to translate rotational motion to the needed linear (e.g., z-direction) motion, thus urging vertical carriage translation element 128 upward or allowing vertical carriage translation element 128 to move downward. Ball screw translation devices are advantaged for handling high weight loads and are typically more efficient than other types of translators using threaded devices. The use of a ball screw arrangement also allows a small motor to drive the shaft that lifts scanner 110 into position and can help to eliminate the need for a complex and bulky counterweight system for allowing control of vertical movement. An encoder 145, such as a linear encoder element, can provide feedback signals that are used to indicate the vertical position of vertical carriage translation element 128.

Vertical carriage translation element 128 travels inside track 112 formed in support column 120 (FIG. 6A); wheels 138 help to guide translation element 128 within the slots. Paired wheels 138 can be orthogonal to each other to provide centering within column 120.

A braking system can also be provided for support column 120. Spring-loaded brakes 142 (FIG. 6D) are positioned to actuate and grip shaft 123 or other mechanical support when mechanical difficulties, power failure, or other conditions are detected. A sensor 144, such as a load cell, is configured to sense rapid movement or interference conditions that are undesirable and to cause brake 142 actuation.

Other features of support column 120 for vertical translation include built-in redundancy, with springs to absorb weight and impact, the load cell to sense a mechanical problem including obstruction by the patient, and manually operable brake mechanisms.

It should be noted that other types of translation apparatus could be used for providing vertical movement of vertical carriage translation element 128. One conventional method for vertical movement control uses a system of pulleys and counterweights to provide lifting force, with motorized assistance. Such an arrangement, however, can be disadvantageous because it can add considerable weight to the column 120 and supporting structure. In spite of its weight-related drawbacks, use of a pulley mechanism can be advantageous for allowing a retractable or telescoping column 120 arrangement, for example, to simplify transport of imaging apparatus 100 between rooms. In one embodiment, the β-axis can be implemented +/−up to 10 degrees. In one embodiment, the horizontal α-axis can be implemented +/−up to 10 degrees. In one embodiment, the γ-axis for a CBCT apparatus can be +/−up to 45 degrees.

Gimbaled Arrangement for Scanner

Forked support arm 130 can support scanner 110 in a gimbaled arrangement. Source 22 and detector 24 are shown on gantry 36 for reference in FIG. 6A and covered in the alternate view of FIG. 6E. Vertical carriage translation element 128 is configured to ride within a track 112 (FIG. 6A) within support column 120.

For certain exemplary embodiments, some level of manual operability can be provided, such as for power loss situations. In one embodiment, forked support arm 130 can be lifted upwards in position by one or more persons, for example, raising vertical carriage translation element 128 even when brakes 142 are set. Shifting support arm 130 upwards does not release the brakes 142, but simply sets the brakes 142 to hold element 128 position at new levels.

According to an alternate embodiment of the application, vertical carriage translation element 128 can be a motor that moves vertically along supporting threaded shaft 132; alternately, vertical carriage translation element 128 can be driven using a chain, pulley, or other intermediate mechanism that has considerable counterweights for manually raising and lowering vertical carriage translation element 128 and its connected forked support arm 130 and components within support column 120. Additional supporting components include a more complex braking system, such as a pneumatic braking system for providing a force opposing gravity in order to prevent sudden movement of forked support arm 130 as a precaution against damage or injury. Vertical carriage translation element 128 can be automated or may be a manually operated positioning device that uses one or more springs or counterweight devices to allow ease of manual movement of forked support arm 130 into position.

Next, considering the α-axis movement of forked support arm 130, in one embodiment a rotational actuator 136 can be energizable to allow rotation of shaft 132 (FIG. 6A). This rotational actuation can be concurrent with z-axis translation as well as with rotation with respect to the γ-axis.

Figure 6E:
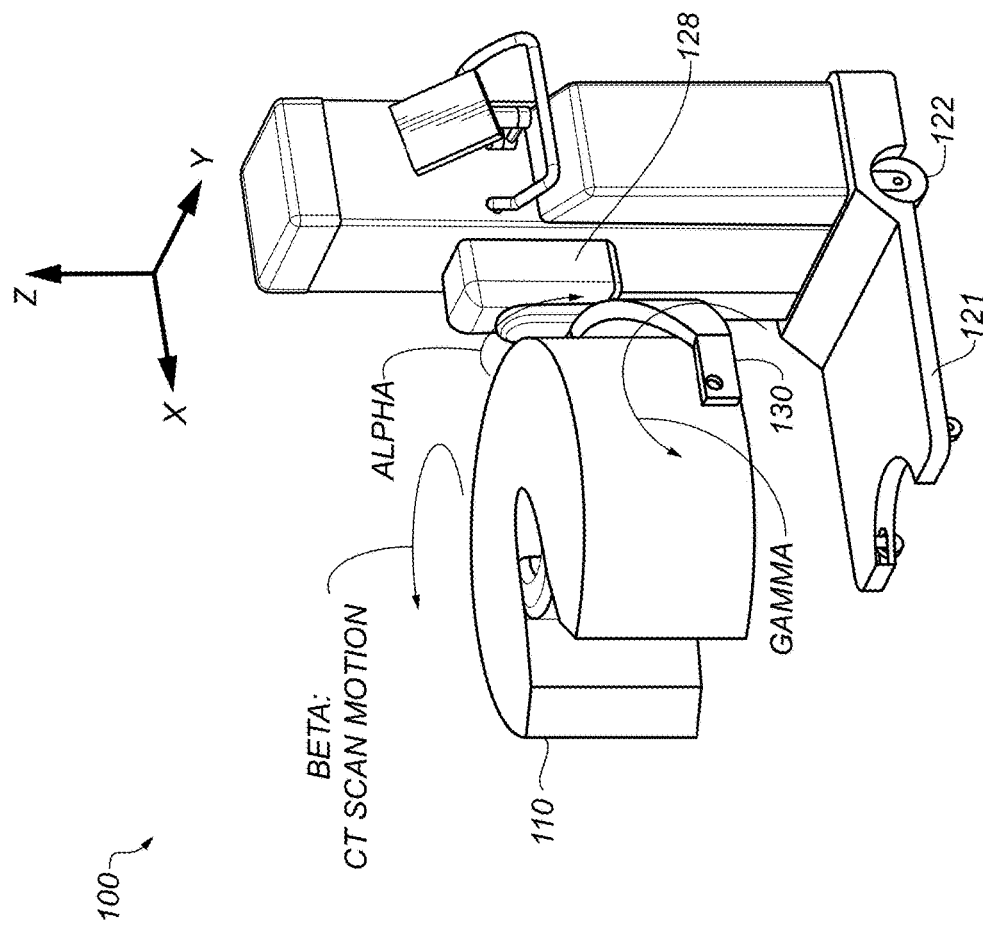
FIG. 6E shows the CBCT imaging apparatus with covers installed.

Forked support arm 130 allows movement relative to the γ-axis according to the position and angle of forked support arm 130. In the example of FIG. 6A, the γ-axis is oriented vertically, substantially in parallel with the z-axis. FIG. 6E shows the γ-axis oriented horizontally. A pivoting mount 140 with a rotational actuator 146, provided by forked support arm 130, allows rotation along the γ-axis. The gimbaled combination of α-axis and γ-axis rotation can allow the imaging apparatus to be set up for imaging in a number of possible positions, with the patient standing, seated, or prone.

Figure 7B:
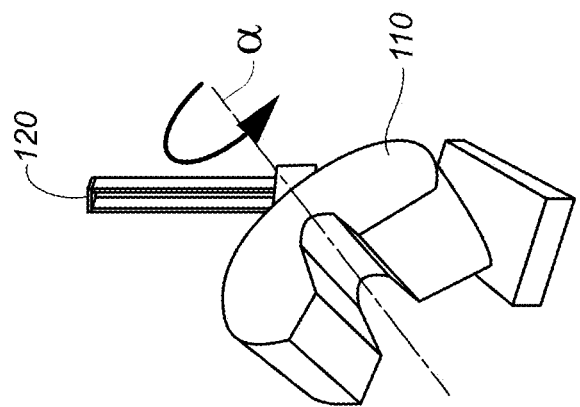
FIG. 7B shows rotation of the imaging ring about an α-axis that is orthogonal to the z-axis.
Figure 7A:
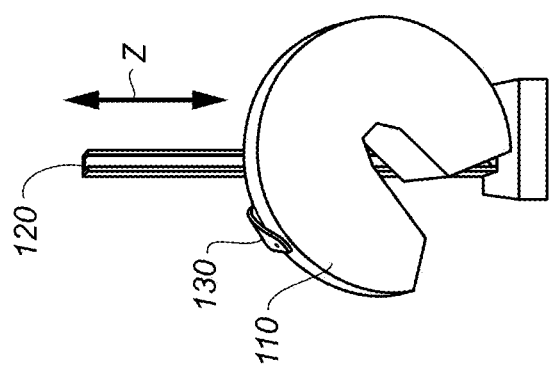
FIG. 7A shows translation of the imaging ring with respect to a vertical or z-axis.
Figure 7C:
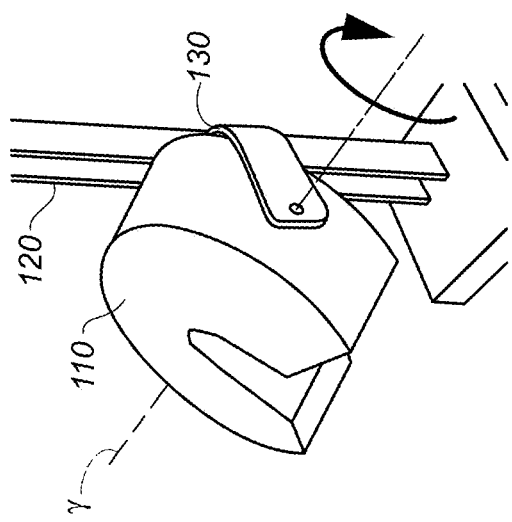
FIG. 7C shows rotation of the imaging ring about a γ-axis that is orthogonal to the α-axis.

An exemplary positioning capability of the imaging apparatus 100 is shown n FIGS. 7A-7C. FIG. 7A shows movement of forked support arm 130 on support column 120 to provide z-axis (vertical) translation of scanner 110. FIG. 7B shows rotation of forked support arm 130 about the horizontal α-axis. FIG. 7C shows rotation about the γ-axis as defined by the C-arm arrangement of forked support arm 130.

Sequence and Controls for Positioning Support Arm 130

According to an embodiment of the present invention, an initial set of operator commands automatically configure CBCT imaging apparatus 100 to one of a well-defined set of default positions for imaging, such as those described subsequently. The patient waits until this initial setup is completed. Then, the patient is positioned at CBCT imaging apparatus 100 and any needed adjustments in height (z-axis) or rotation about the α or γ axes can be made by the technician. This type of fine-tuning adjustment is at slow speeds for increased patient comfort and because only incremental changes to position are needed in most cases.

Figure 7E:
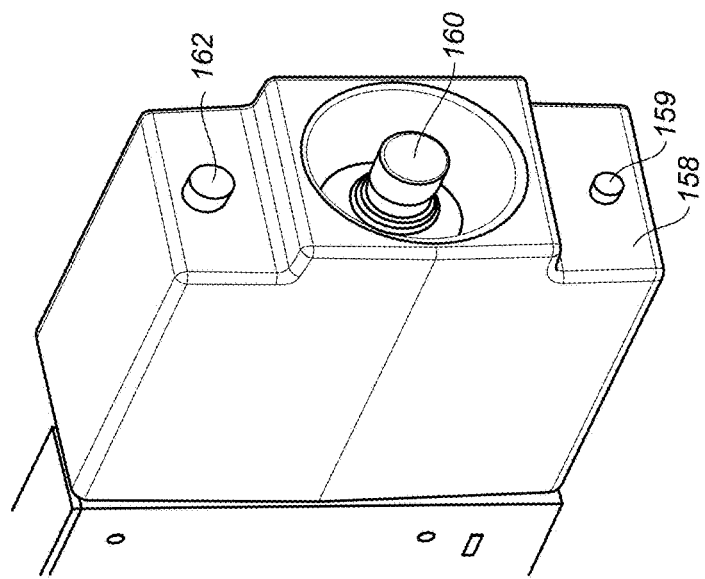
FIG. 7E shows an enlarged view of the positioning controls.
Figure 7D:
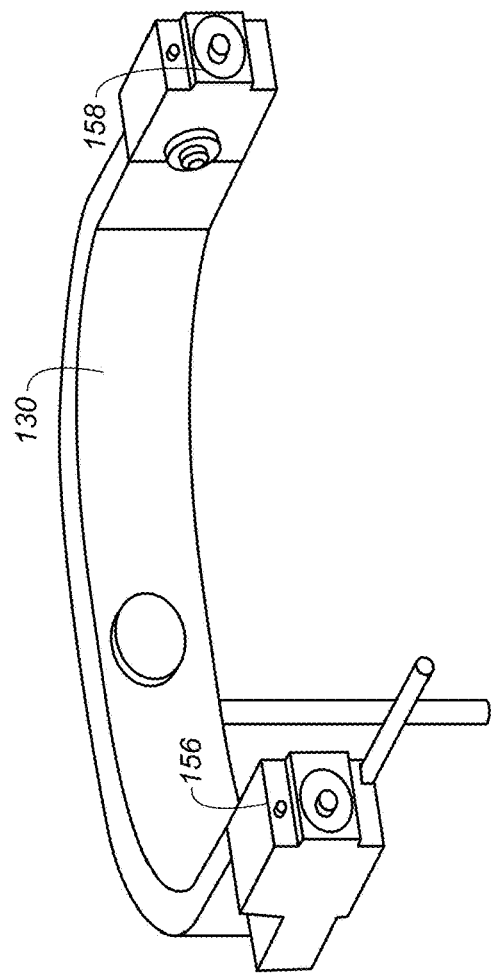
FIG. 7D shows the position of operator controls for fine-tune position of the imaging scanner.

FIG. 7D and the enlarged view of FIG. 7E show user control stations 156, 158 that are provided on arm 130 (with scanner 110 removed for improved visibility) for operator adjustment of z-axis translation and α- and γ-axis rotation as described in FIGS. 7A-7C. Both control stations 156 and 158 are essentially the same, duplicated to allow easier access for the operator for different extremity imaging arrangements. By way of example, FIG. 7E shows an enlarged view of control station 158. An enablement switch 159 is pressed to activate a control 160 and an associated indicator illuminates when control 160 is active or enabled. As a patient safety feature to protect from inadvertent patient contact with the controls in some imaging configurations, one or both control stations 156, 158 are disabled. One or both control stations 156, 158 can also be disabled following a time-out period after switch 159 has been pressed. An emergency stop control 162 can stop all motion of the imaging apparatus including downward motion of support arm 130.

Still referring to FIG. 7E, control 160 can activate any of the appropriate actuators for z-axis translation, α-axis rotation and/or γ-axis rotation. Exemplary responses of the system can be based on operator action, as follows:
  (i) z-axis vertical movement is effected by pressing control 160 in a vertical upward or downward direction. The control logic adjusts for the angular position of the support arm 130, so that pressing the control upward provides z-axis movement regardless of support arm 130 orientation.
  (ii) α-axis rotation is effected by rotating control 160. Circular motion of control 60 in an either clockwise (CW) or counterclockwise (CCW) direction causes corresponding rotation about the α axis.
  (iii) γ-axis rotation is effected by horizontal left-to-right or right-to-left movement of control 60. As with z-axis movement, control logic adjusts for the angular position of the support arm 130, so that left-right or right-left movement is relative to the operator regardless of support arm 130 orientation.

It should be noted that CBCT imaging apparatus 100 as shown in FIG. 6E provides three degrees of freedom (DOF) for scanner 110 positioning. In addition to the z-axis translation and rotation about α- and γ-axes previously described, casters 122 allow rotation of scanner 110 position with respect to the z-axis as well as translation along the floor.

Configurations for Imaging Various Extremities

Given the basic structure described with reference to FIGS. 6A-7D, the positioning versatility of scanner 110 for various purposes can be appreciated. Subsequent FIGS. 8-14 show, by way of example, how this arrangement serves different configurations for extremity imaging.

Figure 8:
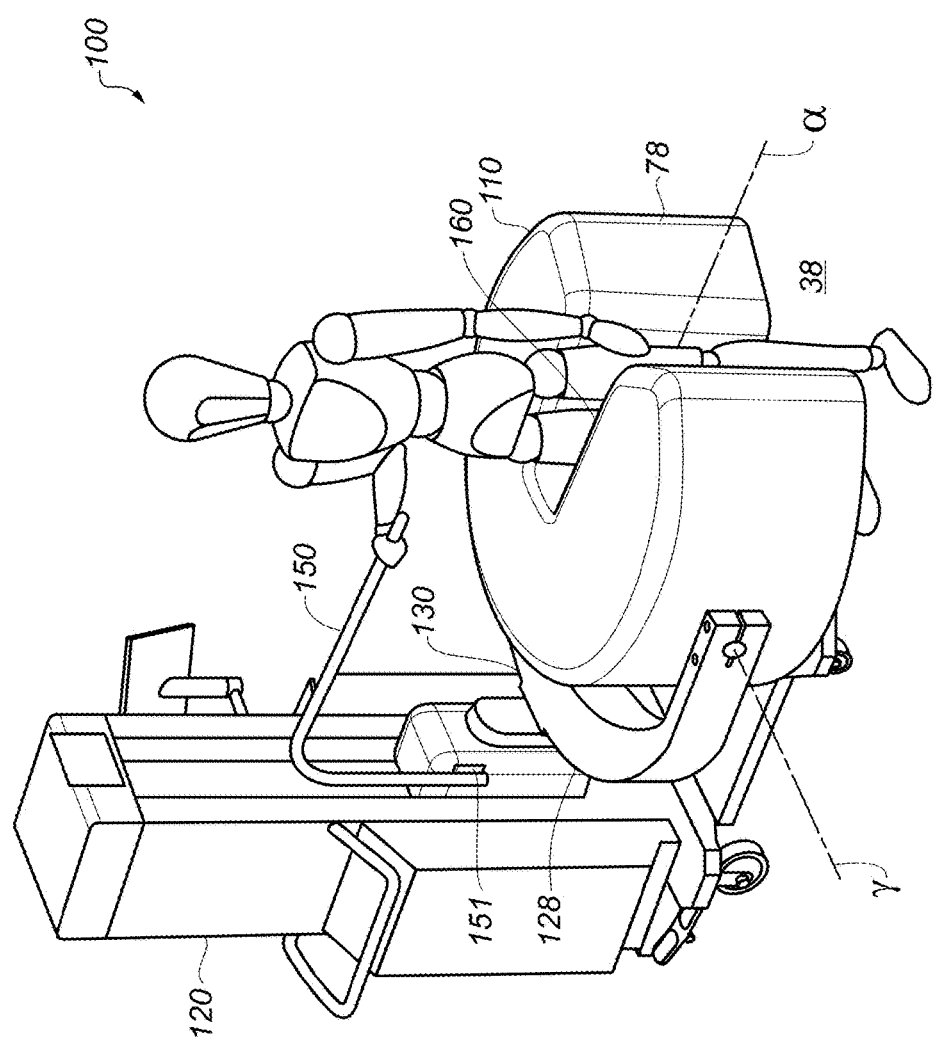
FIG. 8 is a perspective view that shows the extremity imaging apparatus configured for knee imaging with a standing patient.

FIG. 8 shows an exemplary scanner 110 positioning for a knee exam, where subject 20 is a standing patient. An optional patient support bar 150 can be attached to support column 120. In one embodiment, support bar 150 is mounted to vertical carriage translation element 128. Accordingly, as the vertical carriage translation element 128 moves, a corresponding position of the support bar 150 can be moved. According to an alternate embodiment of the application, the support bar 150 can be mounted to the scanner 110, such as to the cover of scanner 110 or to the forked support arm 130. In contrast, embodiments of support bar 150 can be motionless during imaging or during a scan by the scanner 110. For this embodiment, vertical adjustment along the z-axis sets the knee of the patient at the center of the scanner 110. Forked support arm 130 is arranged so that the plane that contains both the α-axis and the γ-axis is substantially horizontal. Patient access is through an opening, circumferential gap or opening 38 in scanner 110. A door 160 is pivoted into place across gap 38 to enclose an inner portion of circumferential gap or opening 38. Door 160 fits between the legs of the patient once the knee of the patient is positioned.

Figure 9:
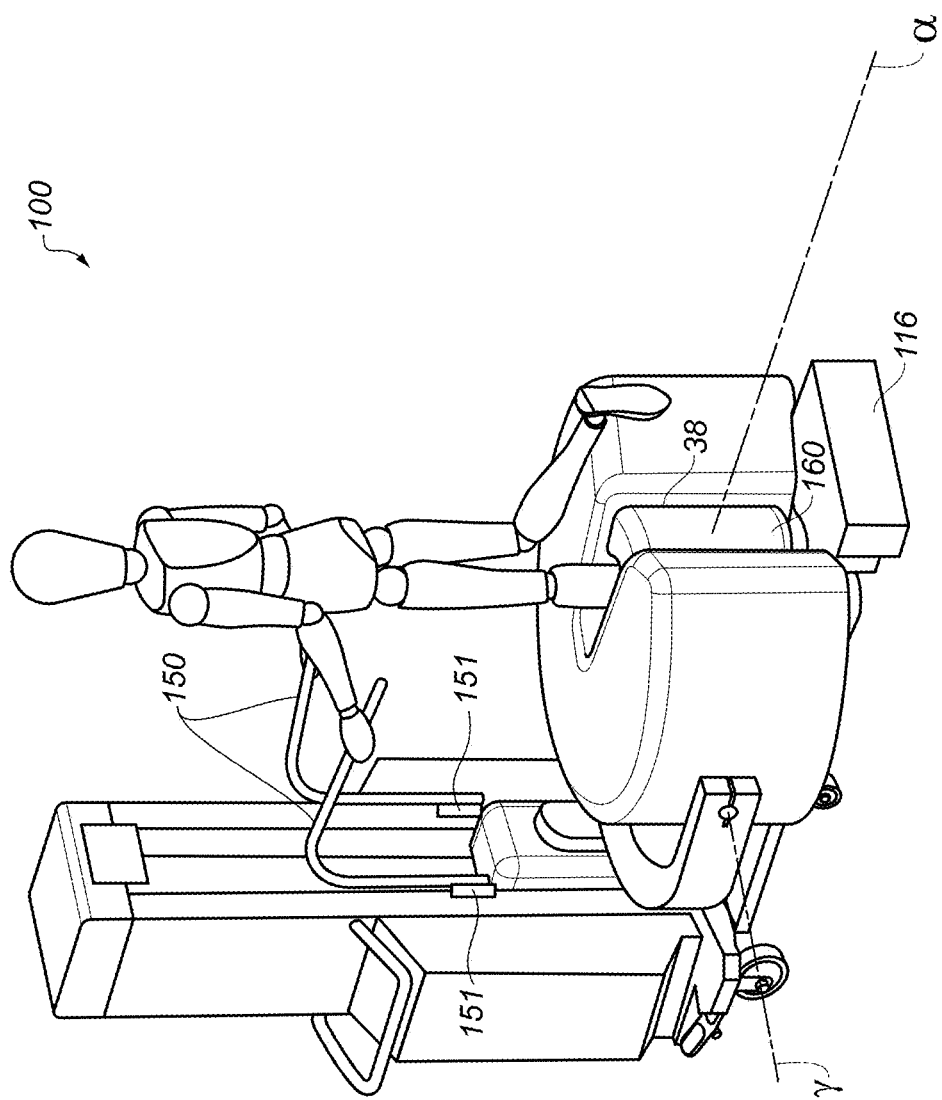
FIG. 9 is a perspective view that shows the extremity imaging apparatus configured for foot or ankle imaging with a standing patient.

Certain exemplary embodiments of optional patient support bar 150 can be mounted to movable portions of the CBCT apparatus 100, preferably to have a prescribed spatial relationship to an imaging volume. For such embodiments, a presence detector 151 can be configured to detect when the support bar 150 is mounted to the CBCT system 100. When detected, a controller or the like, for example, in the control panel 124, can calculate scanner 110, and/or forked support arm 130 movements to prevent collisions therebetween with the affixed support bar 150. Thus, when attached support bar 150 can limit motion of the scanner 110. Exemplary presence detectors 151 can include but are not limited to magnetic detectors, optical detectors, electro-mechanical detectors or the like. As shown in FIG. 9, a pair of optional or removable support arms 150 can be affixed to the vertical carriage translation element 128 and have their attachment reported by a pair of presence detectors 151.

For FIG. 8 and selected subsequent embodiments, door 160, once pivoted into its closed position, can effectively extend the imaging path by protecting and/or providing the curved detector transport 34 path as shown in FIG. 4. With this arrangement, when door 160 is closed to protect the transport path, the knee can be examined under weight-bearing or non-weight-bearing conditions. By enclosing the portion of detector transport 34 path that crosses opening 38, door 160 enables the extremity to be positioned suitably for 3D imaging and to be maintained in position between the source and detector as these imaging components orbit the extremity in the CBCT image capture sequence.

FIG. 9 shows scanner 110 positioning for a foot or ankle exam wherein subject 20 is a standing patient. With this configuration, scanner 110 is lowered to more effectively scan the area of interest. The plane that contains both the α-axis and the γ-axis is approximately 10 degrees offset from horizontal, rotated about the γ axis. A step 116 is provided across circumferential gap or opening 38 for patient access.

Figure 10:
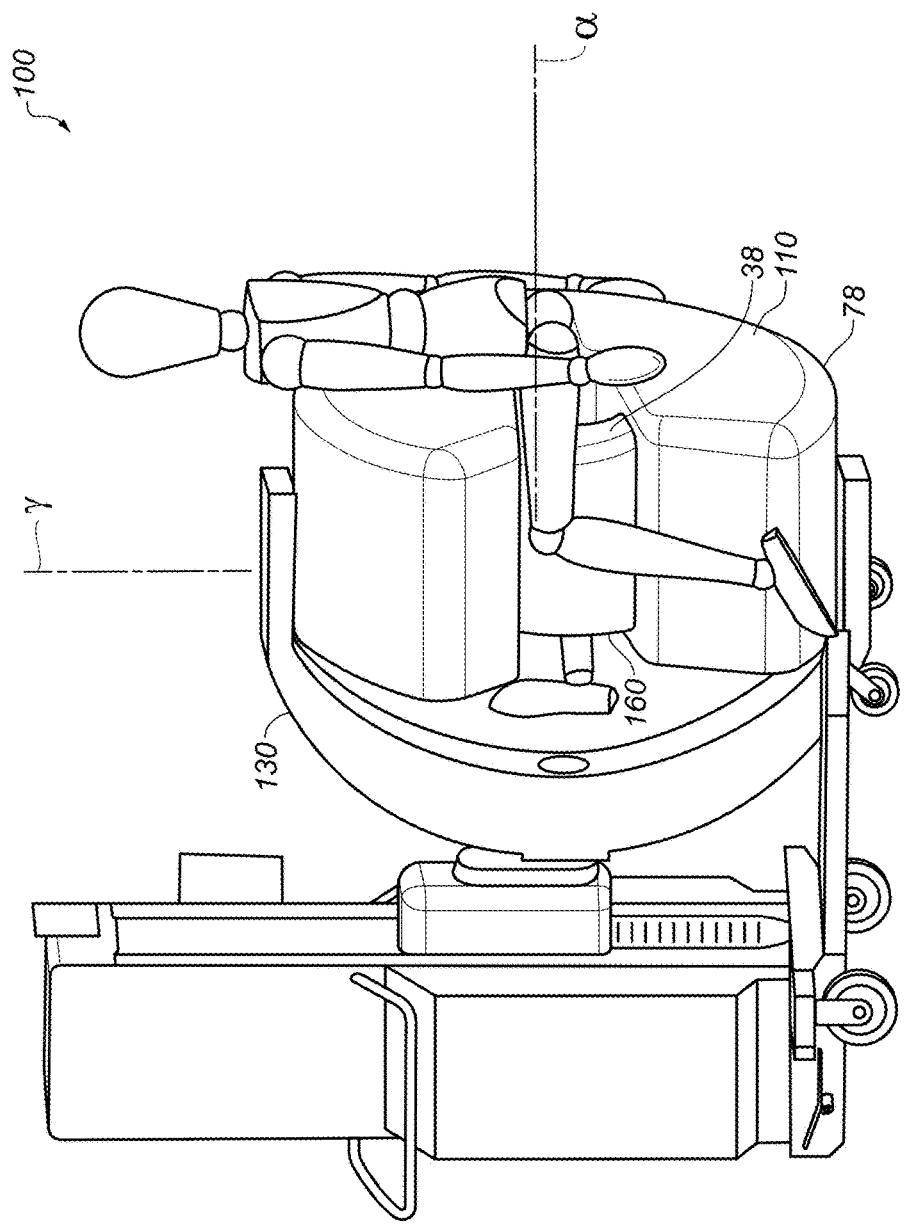
FIG. 10 is a perspective view that shows the extremity imaging apparatus configured for knee imaging with a seated patient.

FIG. 10 shows scanner 110 positioning for a knee exam with the patient seated. For this configuration, forked support arm 130 is elevated with respect to the z-axis. Rotation about the α-axis orients the γ-axis so that it is vertical or nearly vertical. Circumferential gap or opening 38 is positioned to allow easy patient access for imaging the right knee. It should be noted that 180 degree rotation about the γ-axis would position circumferential gap or opening 38 on the other side of scanner 110 and allow imaging of the other (left) knee.

Figure 11:
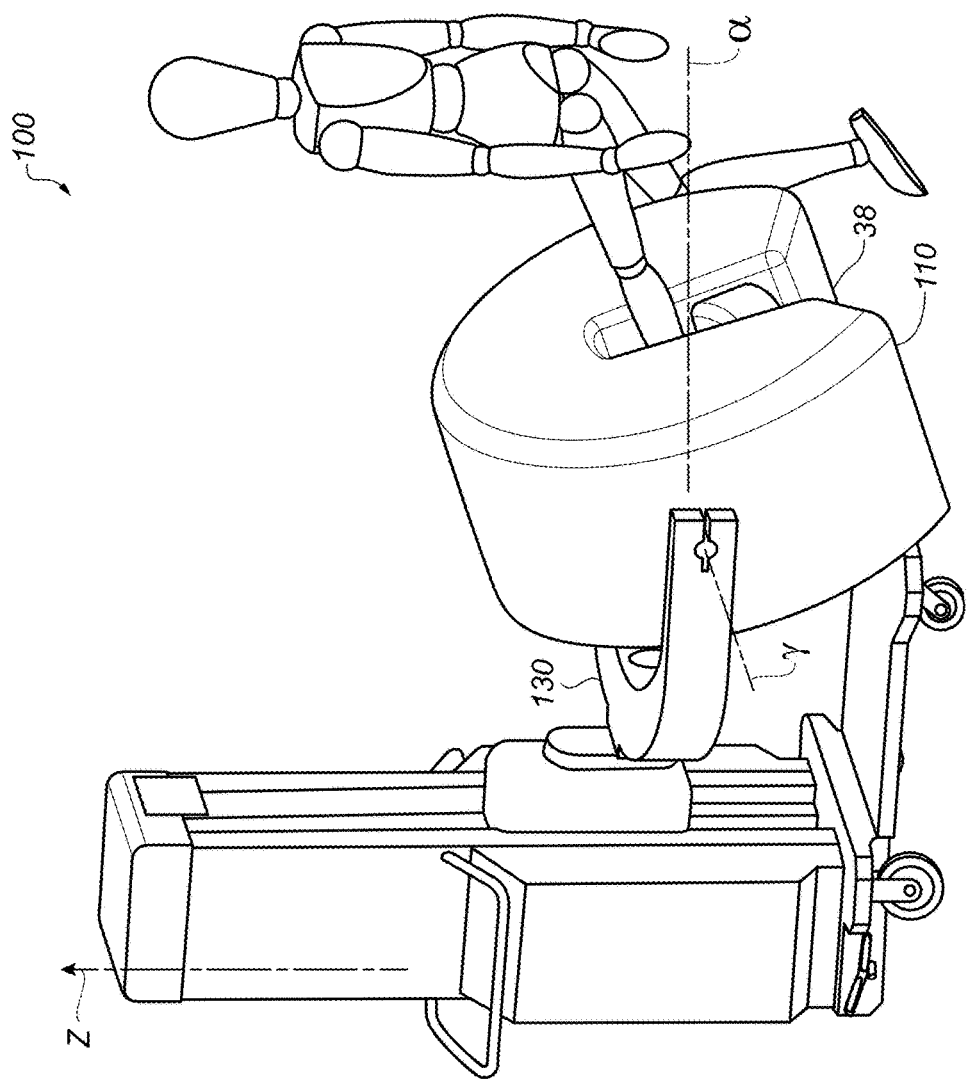
FIG. 11 is a perspective view that shows the extremity imaging apparatus configured for foot or ankle imaging with a seated patient.

FIG. 11 shows scanner 110 positioning for a foot or ankle exam with the patient seated. For this configuration, forked support arm 130 is elevated with respect to the z-axis. Some slight rotation about the α-axis may be useful. Rotation about the γ-axis orients scanner 110 at a suitable angle for imaging. Circumferential gap or opening 38 is positioned for comfortable patient access.

Figure 12:
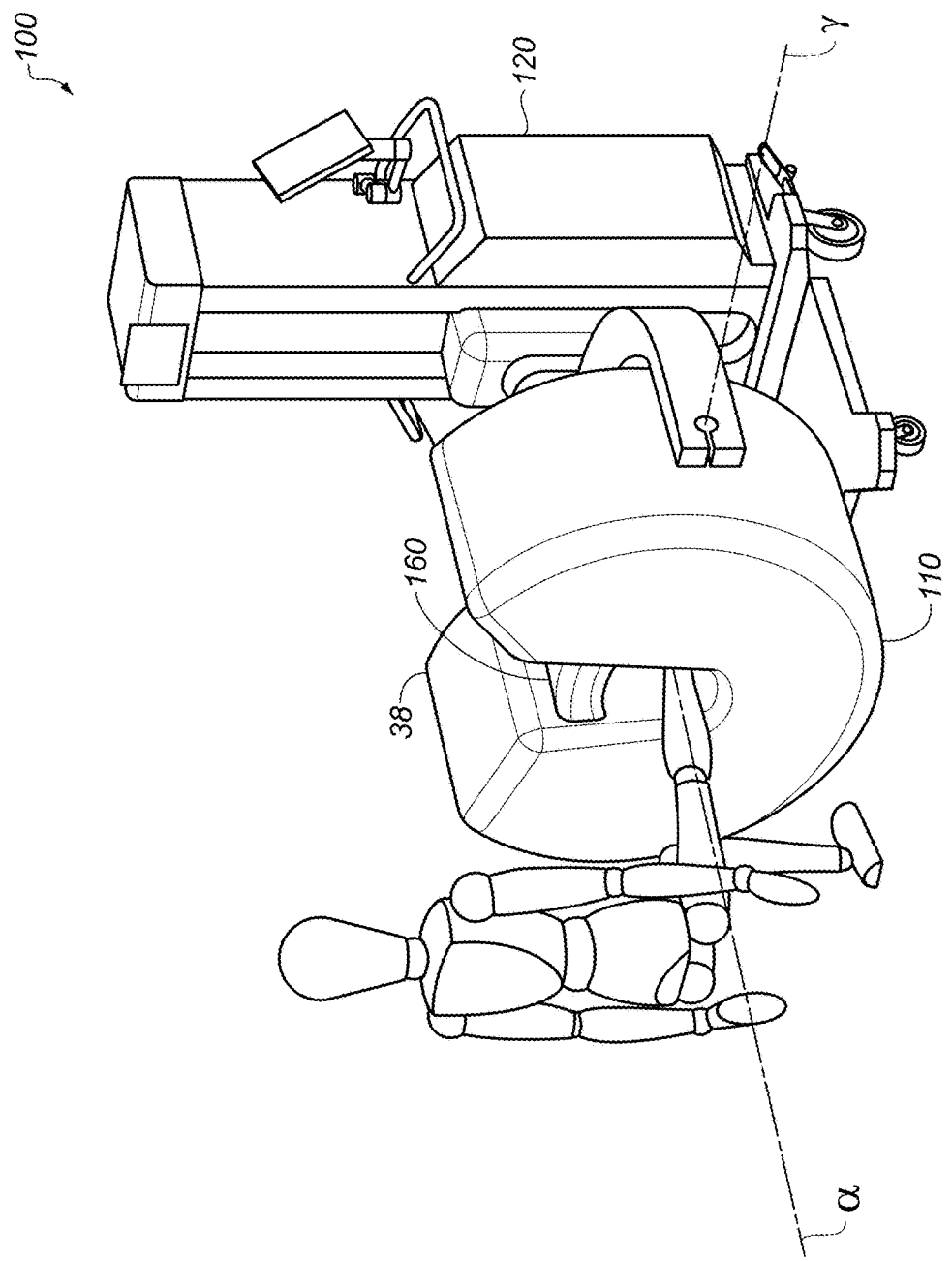
FIG. 12 is a perspective view that shows the extremity imaging apparatus configured for toe imaging with a seated patient.

FIG. 12 shows scanner 110 positioning for a toe exam with the patient seated. For this configuration, forked support arm 130 is elevated with respect to the z-axis. Rotation about the γ-axis positions circumferential gap 38 at the top of the unit for patient access.

Figure 13:
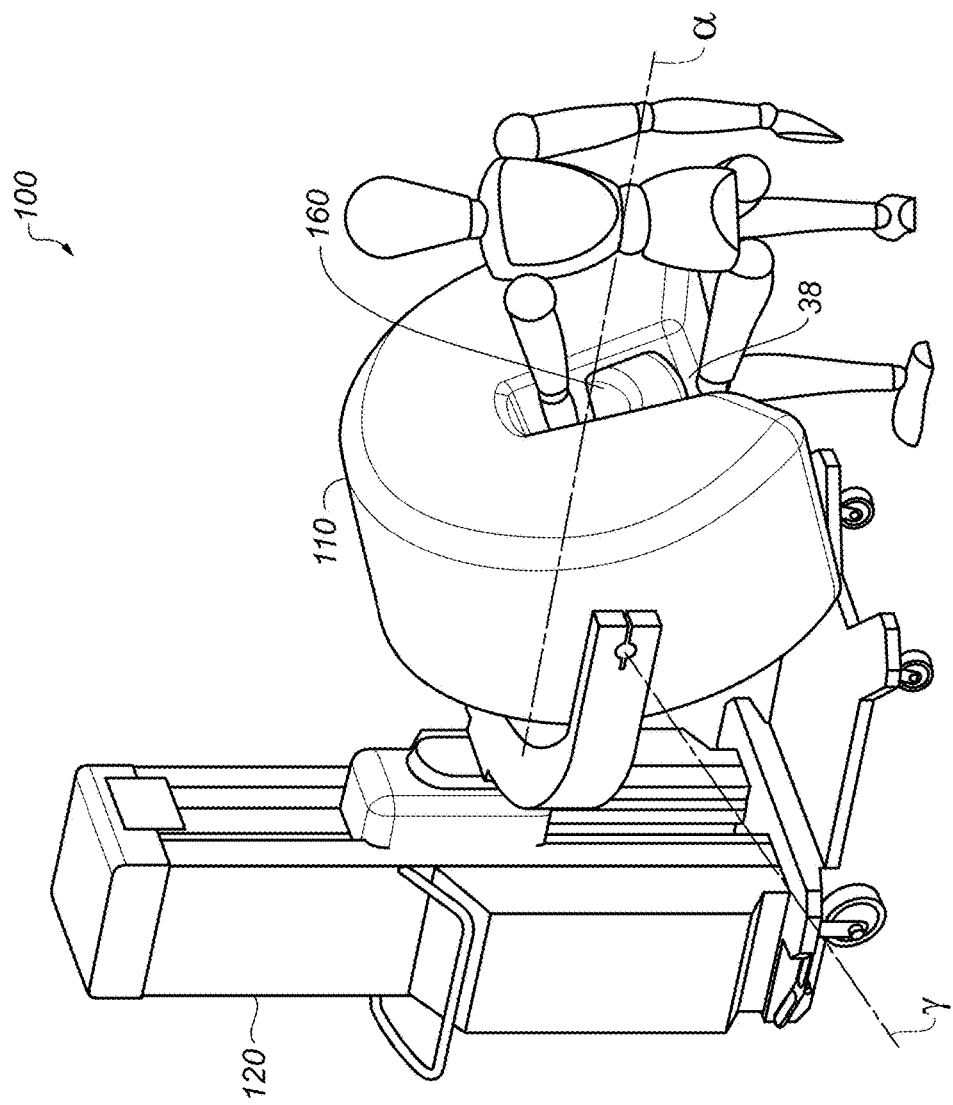
FIG. 13 is a perspective view that shows the extremity imaging apparatus configured for hand imaging with a seated patient.

FIG. 13 shows scanner 110 positioning for a hand exam, with the patient seated. For this configuration, forked support arm 130 is elevated with respect to the z-axis. Rotation about the γ-axis positions circumferential gap 38 suitably for patient access. Rotation about the α-axis may be provided to orient scanner 110 for patient comfort.

Figure 14:
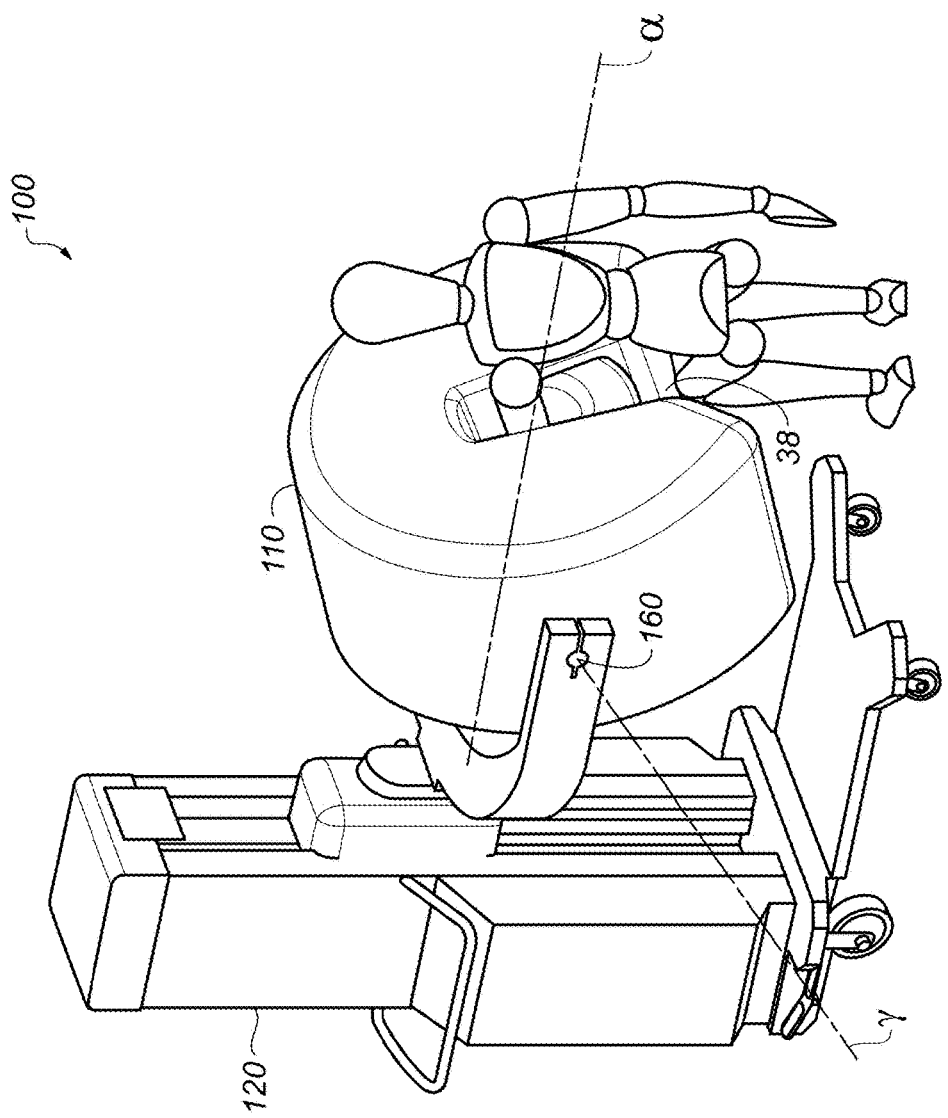
FIG. 14 is a perspective view that shows the extremity imaging apparatus configured for elbow imaging with a seated patient.

FIG. 14 shows scanner 110 positioning for an elbow exam, with the patient seated. For this configuration, forked support arm 130 is again elevated with respect to the z-axis. Rotation about the γ-axis positions circumferential gap 38 suitably for patient access. Further rotation about the α-axis may be provided for patient comfort.

In one embodiment of CBCT imaging apparatus 100, the operator can first enter an instruction at the control console or control panel 124 that specifies the exam type (e.g., for the configurations shown in FIGS. 8-14). The system then automatically adapts the chosen configuration, prior to positioning the patient. Once the patient is in place, manually controlled adjustments to z-axis and α- and γ-axes rotations can be made, as described previously.

Scanner Configuration and Operation

As previously described with reference to FIGS. 1-4, scanner 110 is configured to provide suitable travel paths for radiation source 22 and detector 24 about the extremity that is to be imaged, such as those shown in FIGS. 8-14. Scanner 110 operation in such various exemplary configurations can present a number of requirements that can be at least somewhat in conflict, including the following:

(i) Imaging over a large range of angles, preferably over an arc exceeding 180 degrees plus the fan angle of the radiation source.
(ii) Ease of patient access and extremity positioning for a wide range of limbs.
(iii) Capability to allow both weight-bearing and non-weight-bearing postures that allow imaging with minimized strain on the patient.
(iii) Enclosure to prevent inadvertent patient contact with moving parts.
(iv) Fixed registration of source to detector throughout the scan cycle.

Figure 15A:
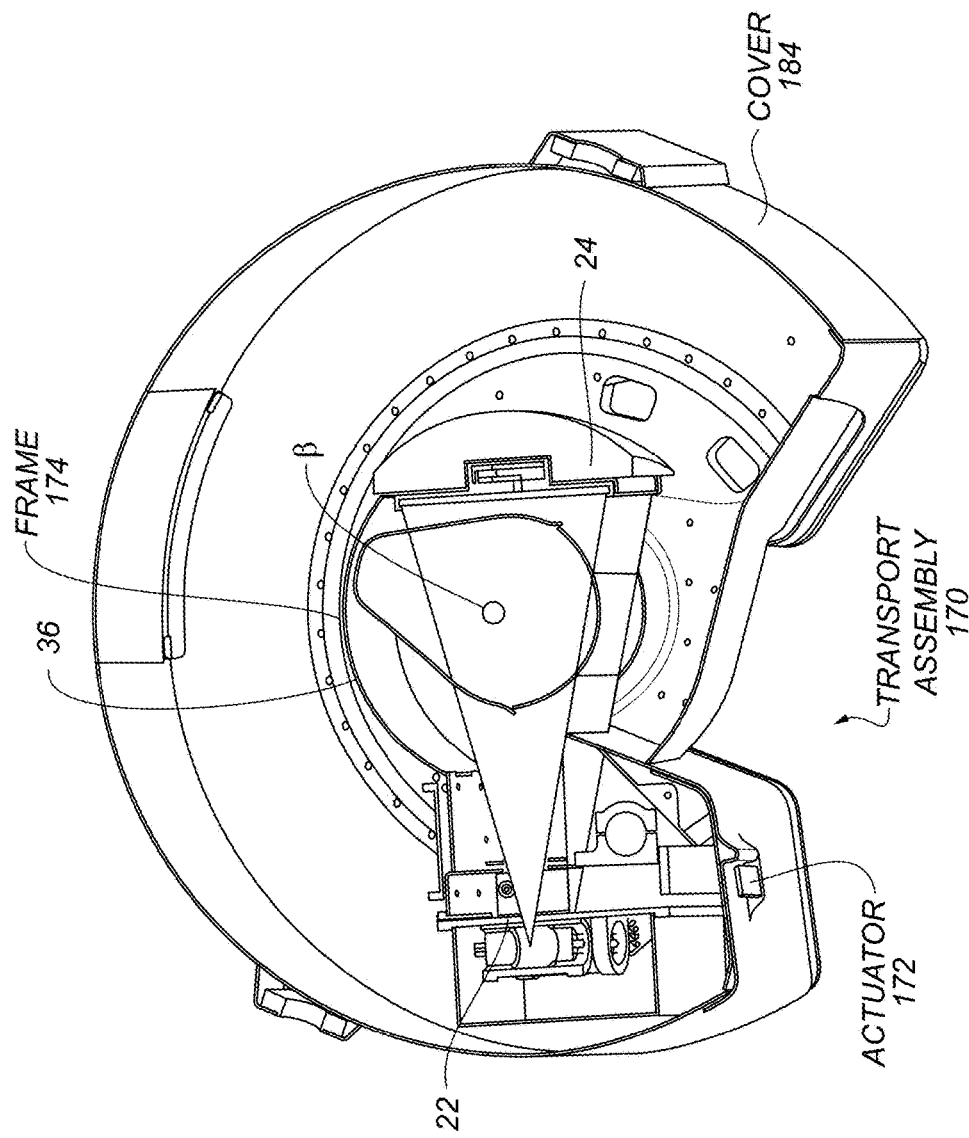
FIG. 15A is a top view of the scanner components of an extremity imaging apparatus according to an embodiment of the application.

The top view of FIG. 15A shows a configuration of components of scanner 110 that orbit subject 20 according to an embodiment of the application. One or more sources 22 and detector 24 are mounted in a cantilevered C-shaped gantry 36 that is part of a transport assembly 170 that can be controllably revolved (e.g., rotatable over an arc about central axis β). Source 22 and detector 24 are thus fixed relative to each other throughout their movement cycle. An actuator 172 is mounted to a frame 174 of assembly 170 and provides a moving hinge for gantry pivoting. Actuator 172 is energizable to move gantry 36 and frame 174 with clockwise (CW) or counterclockwise (CCW) rotation as needed for the scan sequence. Housing 184 can reduce or keeps out dust and debris and/or better protect the operator and patient from contact with moving parts.

Figure 15B:
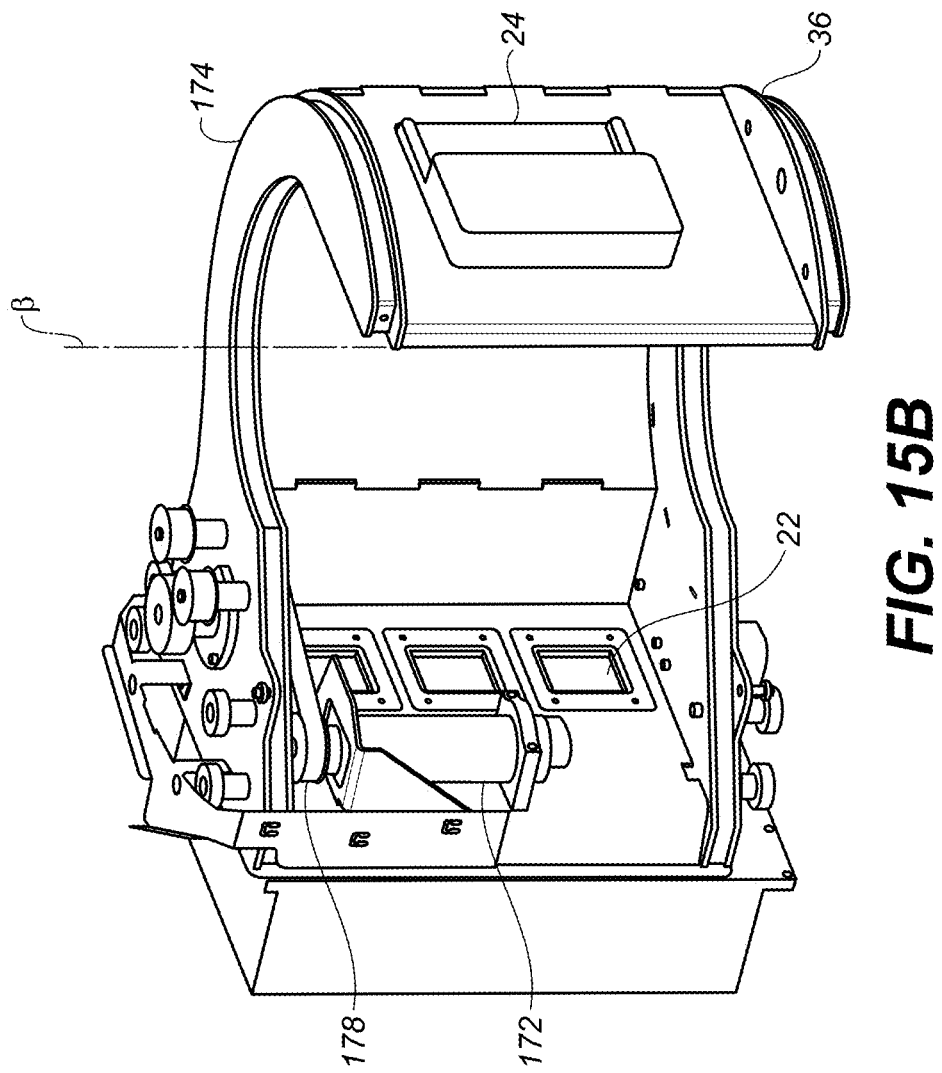
FIG. 15B is a perspective view of a frame that supports scanner components of an extremity imaging apparatus according to an embodiment of the application.
Figure 15C:
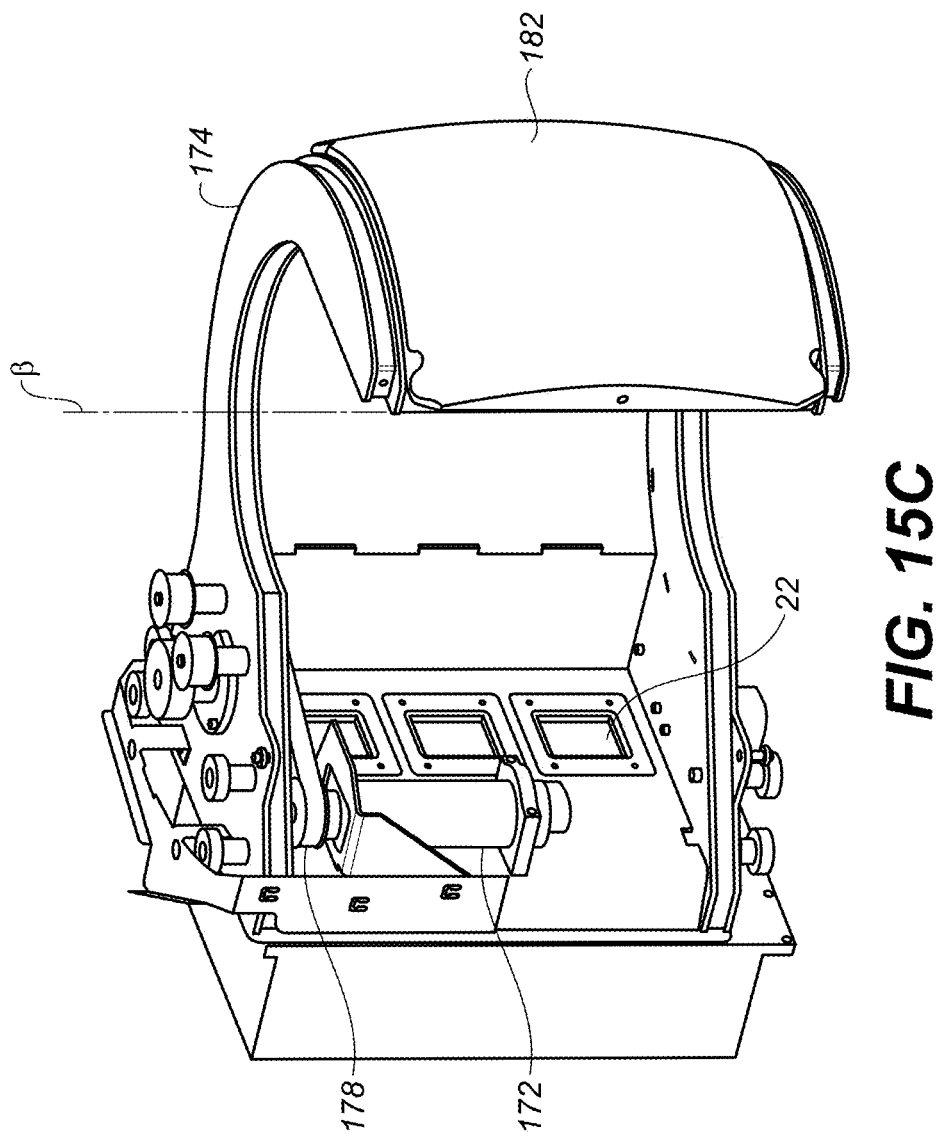
FIG. 15C is a perspective view of a frame that supports scanner components of an extremity imaging apparatus with added counterweight according to an embodiment of the application.

The perspective view of FIG. 15B shows frame 174 and gantry 36 of transport assembly 170 in added detail. Actuator 172 cooperates with a belt 178 to pivot frame 174 for moving source 22 and detector 24 about axis β. The perspective view of FIG. 15C shows frame 174 with added counterweights 182 for improved balance of the cantilevered arrangement.

Because a portion of the scan arc that is detector path 28 (FIG. 2) passes through the circumferential gap or opening 38 that allows patient access, this portion of the scan path should be isolated from the patient. FIGS. 16A, 16B, and 16C show, in successive positions for closing over gap or opening 38, a slidable door 176 that is stored in a retracted position within a housing 180 for providing a covering over the detector path 28 once the patient is in proper position. In one embodiment, door 176 can be substantially a hollow structure that, when closed, allows passage of the detector 24 around the patient's extremity. Referring to FIG. 15B, the portion of frame 174 of gantry 36 that supports detector 24 can pass through the hollow inner chamber provided by door 176 during the imaging scan. At the conclusion of the imaging sequence, frame 174 of gantry 36 rotates back into its home position and door 176 is retracted to its original position for patient access or egress within housing 180. In one embodiment, the door 176 is manually opened and closed by the operator. In one embodiment, interlocks are provided so that movement of scanning transport components (rotation of cantilevered frame 174) is only possible while full closure of the door 176 is sensed.

FIG. 16B also shows top and bottom surfaces 190 and 192, respectively, of housing 180. An outer circumferential surface 194 extends between and connects top and bottom surfaces 190 and 192. An inner circumferential surface 196 is configured to connect the top and bottom surfaces 190 and 192 to form a central opening 198 extending from the first surface to the second surface, where the central opening 198 surrounds the β axis.

As shown with respect to FIGS. 2 and 4, in one embodiment radiation source 22 and detector 24 each can orbit the subject along an arc with radii R2 and R1, respectively. According to an alternate embodiment, within source transport 32, a source actuator could be used, cooperating with a separate, complementary detector actuator that is part of detector transport 34. Thus, two independent actuator devices, one in each transport assembly, can be separately controlled and coordinated by an external logic controller to move source 22 and detector 24 along their respective arcs, in unison, about subject 20.

In the context of the present disclosure, a surface is considered to be "substantially" flat if it has a radius of curvature that exceeds about 10 feet.

The perspective view of FIG. 10 shows the extremity CBCT imaging apparatus 100 configured for knee imaging with a seated patient. From FIG. 10, it can be seen that the patient needs room outside of the scan volume for comfortable placement of the leg that is not being imaged. For this purpose, housing 78 is shaped to provide additional clearance.

As is readily visible from FIGS. 8-14 and 16A-16D, imaging scanner 110 has a housing 78. According to one embodiment of the application, housing 78 is substantially cylindrical; however, a cylindrical surface shape for housing 78 is not required. By substantially cylindrical is meant that, to at least a first approximation, the housing 78 surface shape closely approximates a cylinder, with some divergence from strict geometric definition of a cylinder and with a peripherally gap and some additional features for attachment and component interface that are not in themselves cylindrical.

Figure 17A:
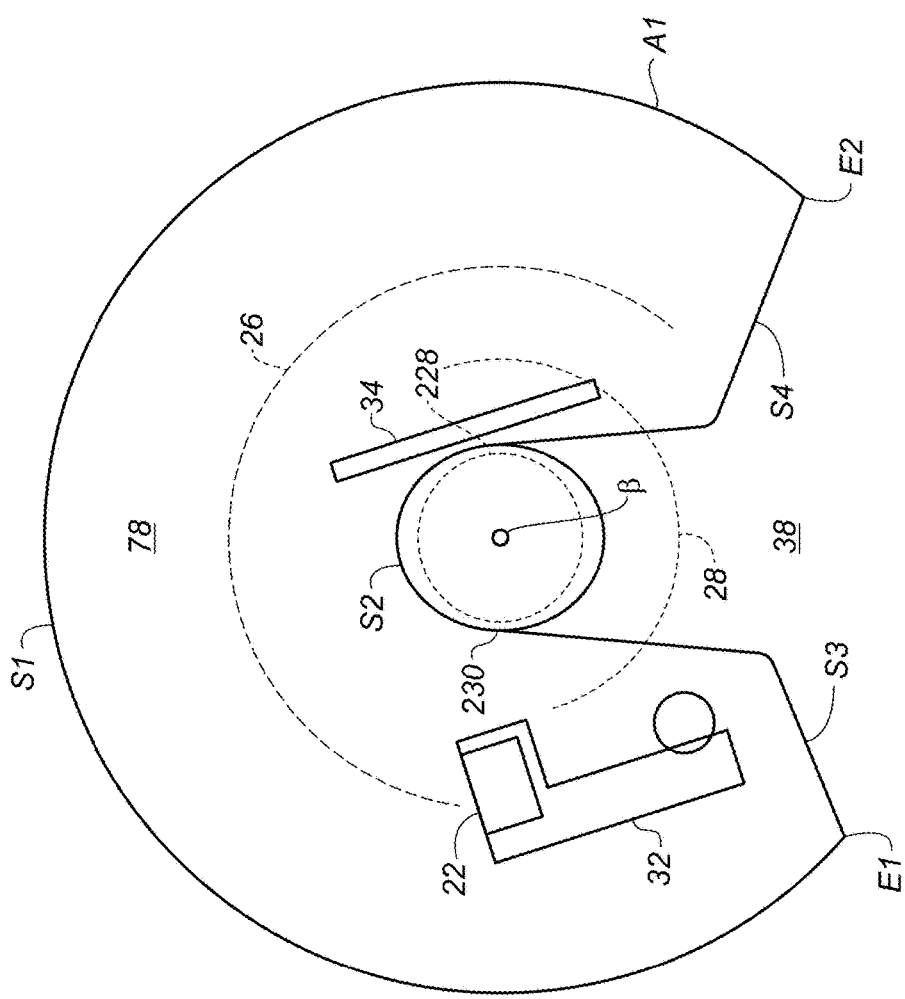
FIG. 17A is a top view of the imaging scanner with a number of its internal imaging components shown, at one extreme end of the imaging scan.
Figure 17B:
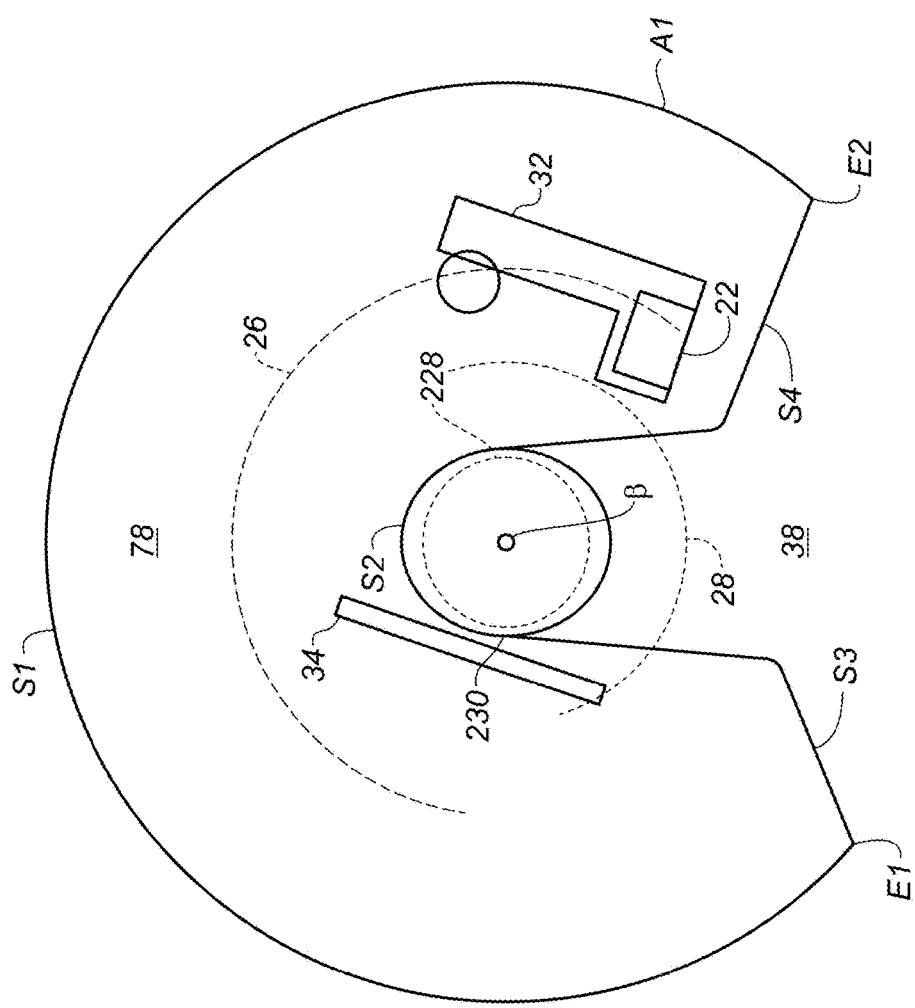
FIG. 17B is a top view of the imaging scanner with a number of its internal imaging components shown, at the opposite extreme end of the imaging scan from that shown in FIG. 17A.
Figure 17C:
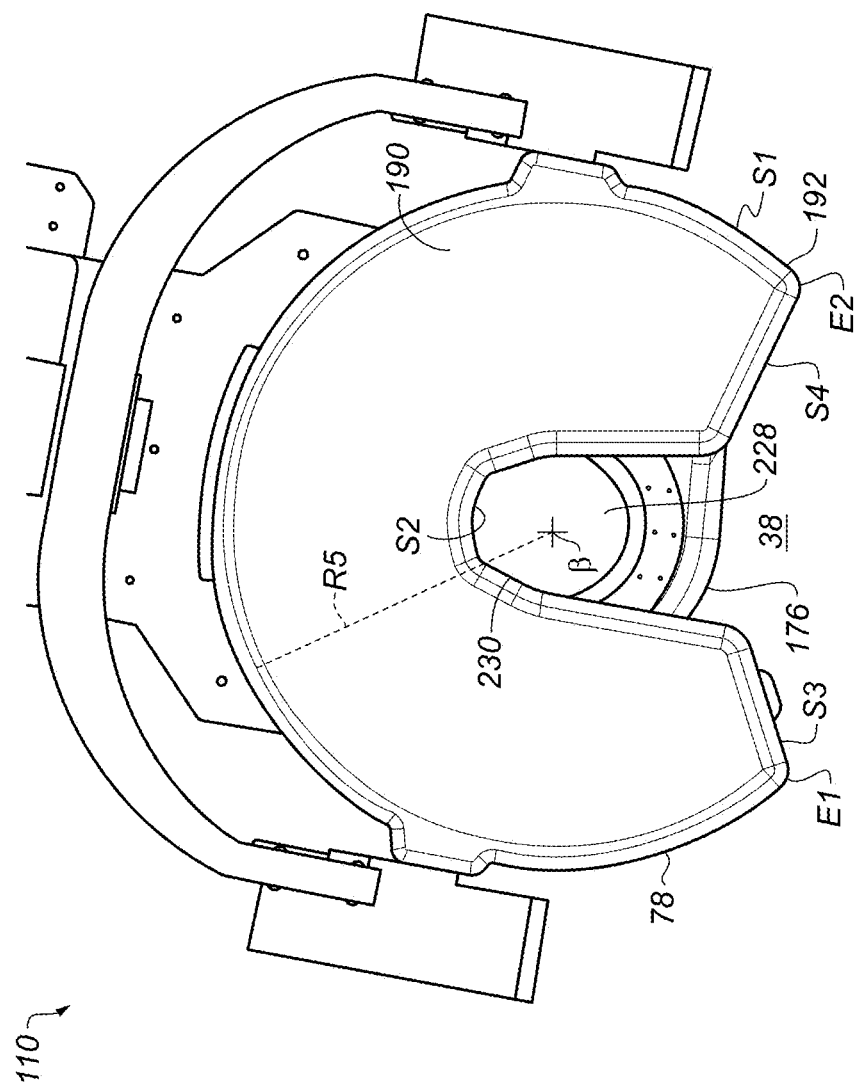
FIG. 17C is a top view of the imaging scanner with its housing shown.

FIGS. 17A-17D show a number of features that are of interest for an understanding of how scanner 110 is configured and operated (e.g., scans). FIG. 17A shows how peripheral gap 38 is formed by housing 78, according to an embodiment of the application. Scan volume 228, outlined with a dashed line, is defined by the source and detector paths 26 and 28, as described previously, and typically includes at least a portion of the β axis. An inner central volume 230 can be defined by surface S2 of housing 78 and can typically enclose scan volume 228. Inner central volume 230 can also be defined by door 176 when closed, as shown in FIG. 17C. Peripheral gap 38 is contiguous with inner central volume 230 when door 176 is in open position (e.g., fully or partially opened).

FIG. 17A shows source transport 32 and detector transport 34 at one extreme end of the scan path, which may be at either the beginning or the end of the scan. FIG. 17B shows source transport 32 and detector transport 34 at the other extreme end of the scan path. It should be noted that source 22 is offset along source transport 32. With this asymmetry, the extent of travel of source 22 relative to surface S3 of housing 78 differs from its extent of travel relative to surface S4. At the extreme travel position shown in FIG. 17B, source 22 is more than twice the distance from surface S4 as source 22 is from surface S3 at the other extreme travel position shown in FIG. 17A. In one embodiment, the inventors use this difference to gain additional clearance for patient positioning with the patient seated.

FIG. 17C shows the configuration of housing 78. In the context of the present disclosure, top surface 190 is considered to be aligned with the top of, at least partially above, or above scan volume 228; bottom surface 192 is aligned with the bottom of, at least partially below, or below scan volume 228. In one embodiment, the top surface 190 or the bottom surface 192 can intersect a portion of the scan volume 228. As shown in FIG. 17C, scan volume 228 can be cylindrical or circularly cylindrical. However, exemplary embodiments of the application are intended to be used with other known 2D scan areas and/or 3D scan volumes. The cover of housing 78 can be metal, fiberglass, plastic, or other suitable material. According to an embodiment, at least portions of top and bottom surfaces 190 and 192 are substantially flat.

As shown in FIGS. 17A-17C, the scanner 110 has a number of surfaces that define its shape and the shape of peripheral gap or opening 38:
   (i) an outer connecting surface S1 extends between a portion of top surface 190 and a portion of bottom surface 192 to at least partially encompass the source and detector; at least a portion of the outer connecting surface extends outside the path the source travels while scanning; embodiments of the outer connecting surface S1 shown in FIGS. 17A-17C provide an arcuate surface that is generally circular at a radius R5 about center β and that extends, between edges E1 and E2 of the housing;
   (ii) an inner connecting surface S2 extends between a portion of the first surface and a portion of the second surface to define an inner central volume 230 that includes a portion of scan volume 228; in the embodiment shown in FIG. 17D, inner connecting surface S2 is approximately at a radius R4 from the β axis. At least portions of inner connecting surface S2 can be cylindrical.
   (iii) other connecting surfaces can optionally include a surface S3 that corresponds to a first endpoint of the travel path for source transport 32 (FIGS. 17A-17B) and is adjacent to curved surface S1 along an edge E1, wherein surface S3 extends inward toward curved inner surface S2; and a surface S4 that corresponds to a second endpoint at the extreme opposite end of the travel path from the first endpoint for source transport 32 and is adjacent to curved surface S1 along an edge E2 wherein surface S4 extends inward toward curved inner surface S2. According to an embodiment, surfaces S3 and S4 are substantially flat and the angle between surfaces S3 and S4 is greater than about 90 degrees. In general, other additional surface segments (e.g., short linear or curved surface segments) may extend between or comprise any of surfaces S1-S4.

Figure 17D:
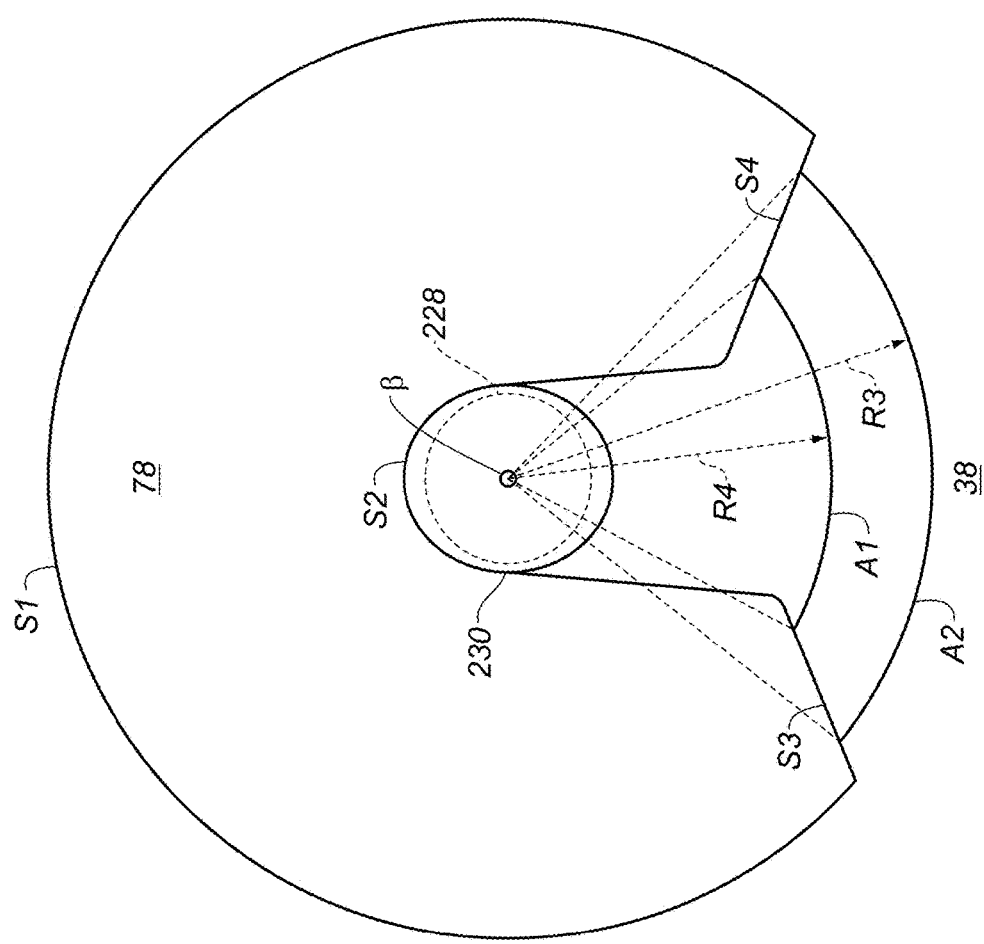
FIG. 17D is a top view of the imaging scanner with internal imaging components and central arc angles shown.

Inner and outer connecting surfaces S1, S2, and, optionally, other surfaces, define peripheral gap or opening 38 that is contiguous with the inner central volume 230 and extends outward to intersect the outer connecting surface S1 to form gap 38 as an angular recess extending from beyond or toward where the outer connecting surface S1 would, if extended, cross the opening 38. As shown in FIG. 17D, a central angle of a first arc A1 that is defined with a center located within the scan volume and between edges of the peripheral gap 38 determined at a first radial distance R4 outside the scan volume is less than a central angle of a second arc A2 that is defined with the first arc center and between the edges of the peripheral gap 38 at a second radial distance R3 outside the scan volume, where the second radial distance R3 is greater than the first radial distance R4. In one embodiment, as shown in FIG. 17D, a first distance that is defined between edges of the peripheral gap 38 determined at a first radial distance R4 outside the scan volume is less than α second distance between the edges of the peripheral gap 38 at a second radial distance R3 outside the scan volume, where the second radial distance R3 is greater than the first radial distance R4. According to one embodiment, arcs A1 and A2 are centered about the β axis, as shown in FIG. 17D and edges of gap 38 are defined, in part, by surfaces S3 and S4 of housing 78.

The needed room for patient anatomy, such as that described with reference to FIG. 10, can be provided when the central angle for arc A2 is large enough to accommodate the extremity that is to be imaged. According to one embodiment, the central angle for arc A2 between edges of gap 38 exceeds the central angle for arc A1 by at least about 5 degrees; more advantageously, the central angle for arc A2 exceeds the central angle for arc A1 by at least about 10 or 15 degrees.

The perspective views of FIGS. 8-14 show various configurations of extremity CBCT imaging apparatus 100 for imaging limbs of a patient. For each of these configurations, the limb or other extremity of the patient must be positioned at the center of scanner 110 and space must be provided for the paired extremity. As described herein, peripheral gap or opening 38 is provided to allow access space for the patient and room for other parts of the patient anatomy. Door 176 is withdrawn into the housing 78 until the patient is positioned; then, door 176 is pivoted into place in order to provide a suitable transport path for the imaging receiver, detector 24, isolated from the patient being imaged.

Figure 16D:
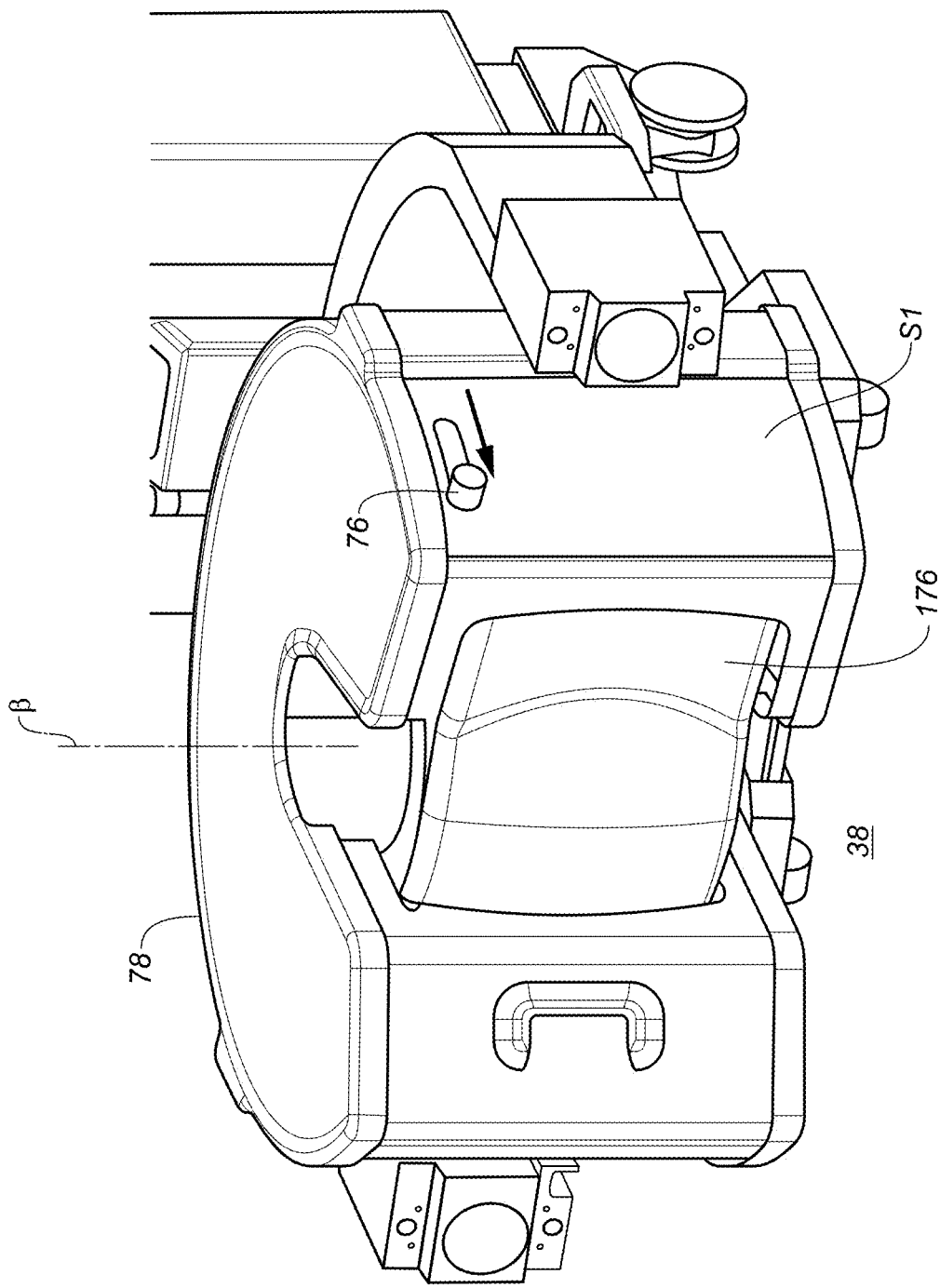
FIG. 16D is a perspective view showing the door in closed position.

FIG. 16A shows scanner 110 with door 176 in open position, not obstructing opening 38, that is, keeping opening 38 clear, allowing patient access for extremity placement within opening 38. FIG. 16C is a top view that shows scanner 110 with door 176 in closed position, held by a latch 92. Door 176 thus extends into the opening 38, enclosing a portion of opening 38 for imaging of the patient's extremity. A sensor 82 provides an interlock signal that indicates at least whether door 176 is in closed position or in some other position. Movement of internal scanner 110 components such as c-shaped gantry 36 is prevented unless the door 176 is latched shut. A release 90 unlatches door 176 from its latched position. As shown in FIGS. 16C and 16D, handle 76 can be positioned outside of opening 38, such as along surface S1 as shown, for opening or closing door 176. Placement of handle 76, or other type of door closure device, outside of opening 38 is advantageous for patient comfort when closing or opening door 176. As shown in the exemplary embodiment of FIGS. 16C and 16D, handle 76 is operatively coupled with door 176 so that movement of handle 76 in a prescribed direction, such as along the circumference of scanner 110 housing 78 (e.g., a corresponding direction, or in the clockwise direction shown), causes door 176 corresponding movement (e.g., in the same direction). In one embodiment, clockwise movement of handle 76 causes clockwise movement of door 176, extends door 176 into the opening, and closes door 176; counter-clockwise movement of handle 76 causes counterclockwise movement of door 176 and opens door 176, so that it does not obstruct the opening or moves to a position that is clear of the opening.

According to one embodiment, the door 176 is manually pivoted, closed, and opened by the operator. This allows the operator to more carefully support the patient and the extremity that is to be imaged. According to an alternate embodiment, an actuator is provided to close or open the door automatically.

FIG. 18A is a cross-section view that shows the shape of door 176 in position within housing 78 from a side view. As can clearly be seen in this figure, door 176 is substantially hollow; its function is to provide a protective shell or covering that isolates the patient from the detector and protects the patient against inadvertent contact with moving parts of the scanning mechanism. With this arrangement, door 176 provides a hollow passage 84 for the detector 24 during an imaging scan. An inner surface 96, facing the inner portions of housing 78, preferably maintains the cylindrical shape of a scan chamber 228 within scanner 110. According to an embodiment of the present invention, hollow passage 84 is substantially tubular.

Figure 18D:
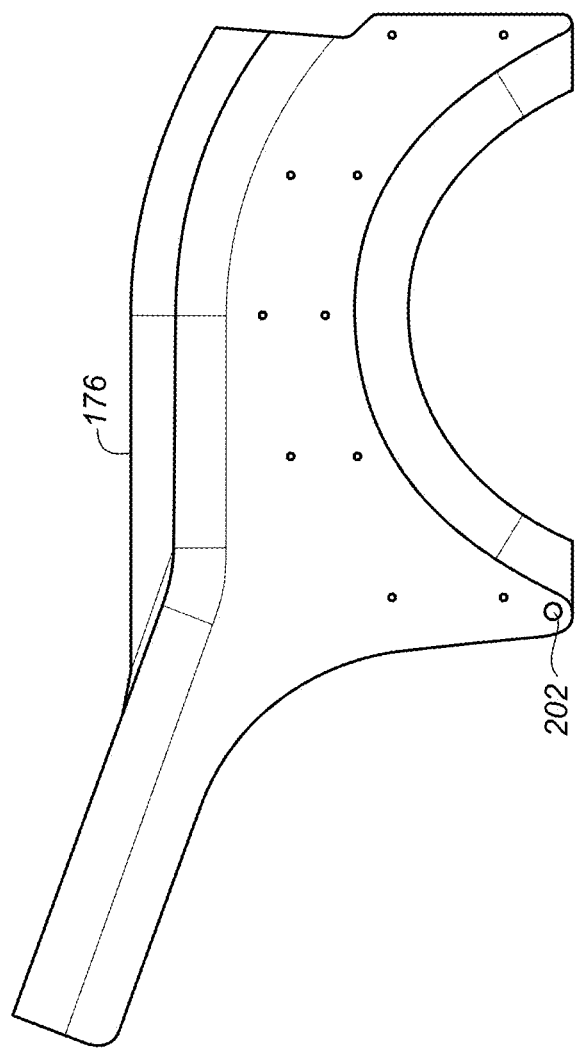
FIG. 18D is a top view of the door.

The design of door 176 has a number of features that help to improve patient comfort and use of extremity CBCT imaging apparatus 100. One feature relates to the cross-sectional shape of door 176, or of at least a portion of door 176 (e.g., an outside surface), as shown in the cross-section view of FIG. 18B. Door 176 is tapered so that it is wider in its middle section and narrows in the direction of central axis β. Thus, door 176 is cross-sectionally barrel-shaped or wedge-shaped. According to another alternate embodiment, a portion of door 176 is notched or otherwise featured to provide a more suitable profile for positioning the patient. without obstructing the internal hollow passage 84. In one embodiment, radially outside portions of the door 176 can be narrowed to increase object positioning room and can include an elastic or foam type materials (e.g., without obstructing the detector path). FIG. 18B shows the tapering of the door outline in cross section, where width w2 is reduced from width w1 by at least about 5%. In one embodiment, width w2 is reduced from width w1 by at least about 30-50%. FIG. 18C is a perspective view of the door showing hollow passage 84 with dashed line to indicate the detector path 28 through the door and a closure portion 188, described in more detail subsequently. FIG. 18D is a top view of the door 176, showing a pivot point 202 on which door 176 pivots into open or closed position. Preferably, the tapering of the door 176 is configured to outside surfaces/shapes to preferably maintain a corresponding shape to the remaining imaging bore yet reduce outer cross-sectional dimensions for patient ease.

FIGS. 19A through 19D show, from a top view, the relative angular rotation of gantry 36 as it pivots about the β axis at different angular intervals in the scan sequence and how the hollow passage 84 provided by door 176 allows a wide angular range of travel for the orbit of detector 24 around the subject being imaged within the scan volume 228. This sequence shows how door 176 covers or surrounds, but does not obstruct, detector path 28 and shows how detector path 28 passes through the hollow interior of door 176 for imaging when the patient is appropriately positioned and door 176 is pivoted into place and latched.

Figure 19A:
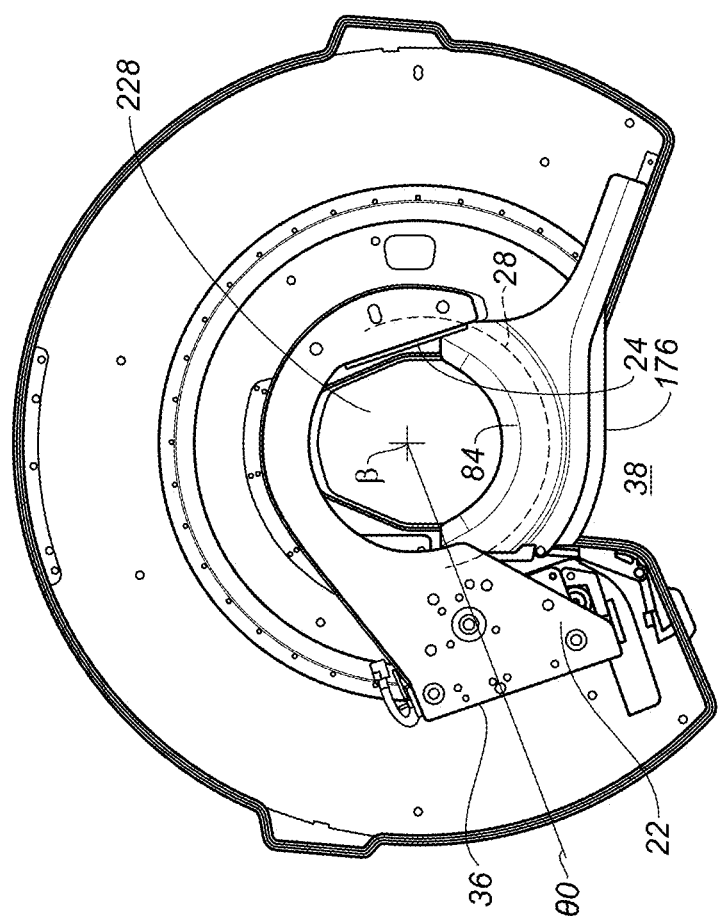

FIG. 19A shows the initial position of gantry 36 at an angle θ0 when door 176 has just been closed. Source 22 and detector 24 are at a rest or default position at angle θ0. Detector path 28 extends into the hollow portion of door 176 as shown.

Figure 19B:
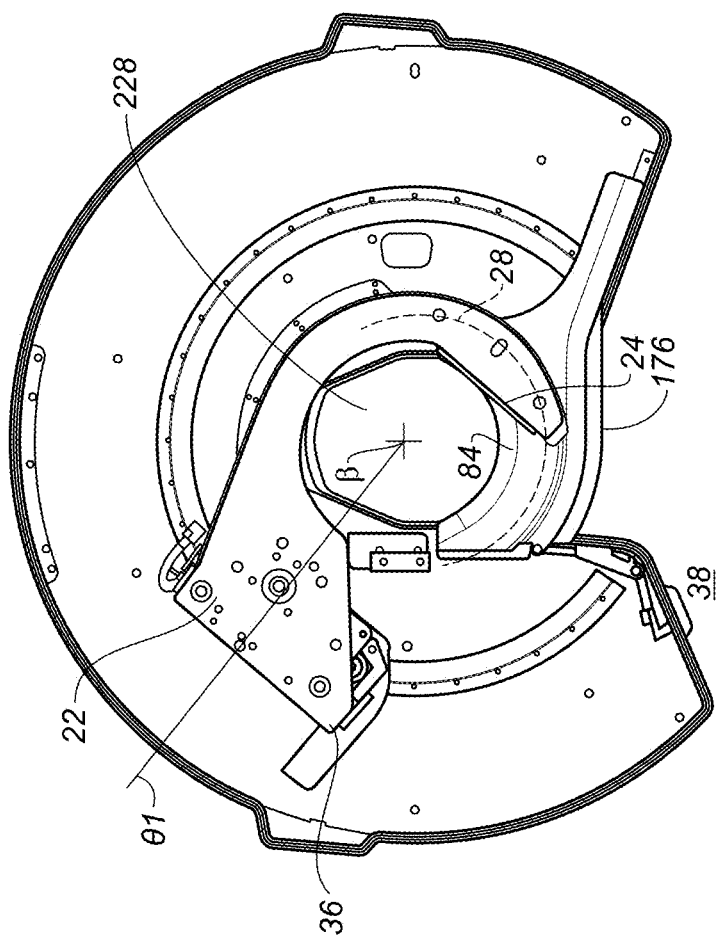

FIG. 19B shows gantry 36 rotated to a second angle θ1 during imaging, at an early portion of the scan. A portion of detector 24 now extends into hollow passage 84 of door 176.

FIG. 19C shows gantry 36 rotated to a third angle θ2 as the scan continues. Detector 24 now extends back into housing 78, through door 176.

Figure 19D:
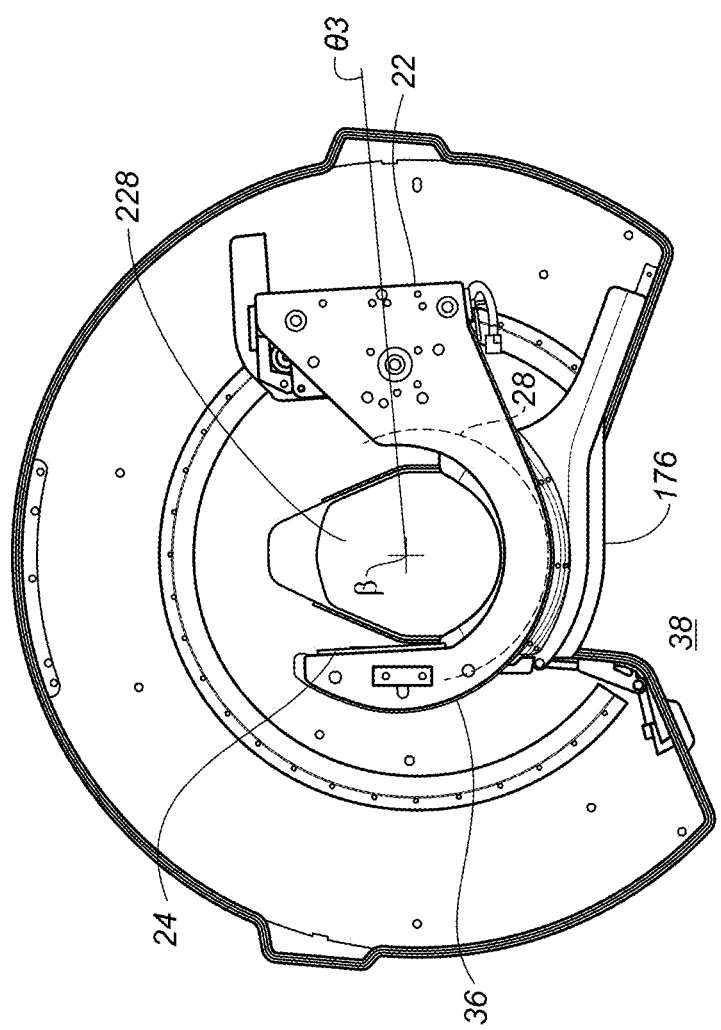

FIG. 19D shows gantry 36 rotated to a fourth angle θ3 near the end of its scan path. Detector 24 now extends past door 176 and into housing 78.

Once the imaging sequence is complete, gantry 36 rotates back to its rest position (FIG. 19A) so that door 176 can be opened for patient egress from opening 38.

As the sequence of FIGS. 19A-19D shows, the configuration of door 176 with hollow passage 84 protects, but does not obstruct, detector path 28 allows C-shaped gantry 36 travel over a considerable range of angles. It should be noted that the full range of angular travel may not be needed for imaging in a particular case. It should also be observed that FIGS. 19A-19D show gantry 36 rotation in a clockwise (CW) direction; rotation of gantry 36 for imaging could alternately be in a counter-clockwise (CCW) direction, proceeding from angle θ3 to angle θ0 according to an alternate embodiment of the present invention.

As noted previously, an interlock arrangement is provided, preventing movement of C-shaped gantry 36 unless the door 176 is fully closed across the opening 38. According to an alternate embodiment, an operator override is provided so that scan operation is permitted from a position with door 176 partially open.

Figure 20B:
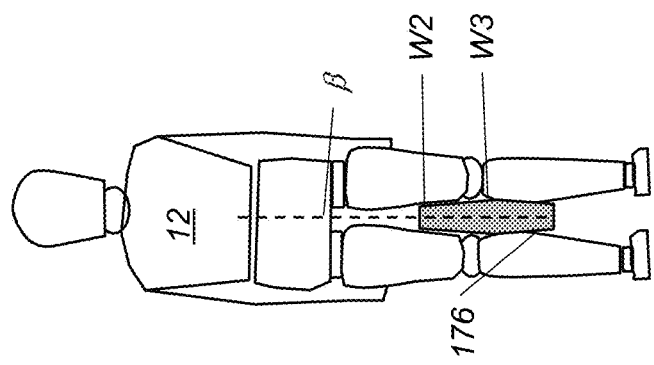
FIGS. 20A and 20B show schematic views that show the effect of door shape on patient stance.
Figure 20A:
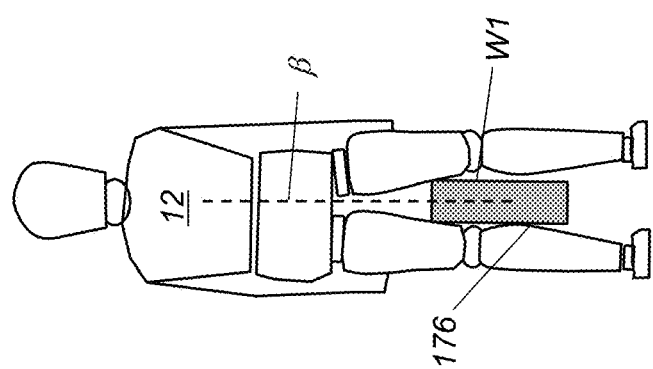

FIGS. 20A and 20B show, slightly exaggerated for emphasis, the advantages for patient comfort and positioning provided by the curved shape or barrel-shaped profile of door 176, relative to standing posture of a patient 12. Widths W1, W2, and W3 are measured in a direction that is orthogonal to central axis β. Narrowed width W2 over at least some portion of the door 176 as shown in FIG. 20B provides room for the patient's knees or calves and allows a more natural standing posture during imaging. For this purpose, width W2 is smaller than width W3 by at least about 10%. If walls of door 176 were straight, that is, of the same width W1 without a narrower portion W2 as in FIG. 20A, patient positioning for a number of types of exams would be less natural and less comfortable for a number of patients.

According to an alternate embodiment, another feature of door 176 is a closure portion 188 that can cover a door aperture 88 in housing 78 before, during and following door closing.

Figure 21:
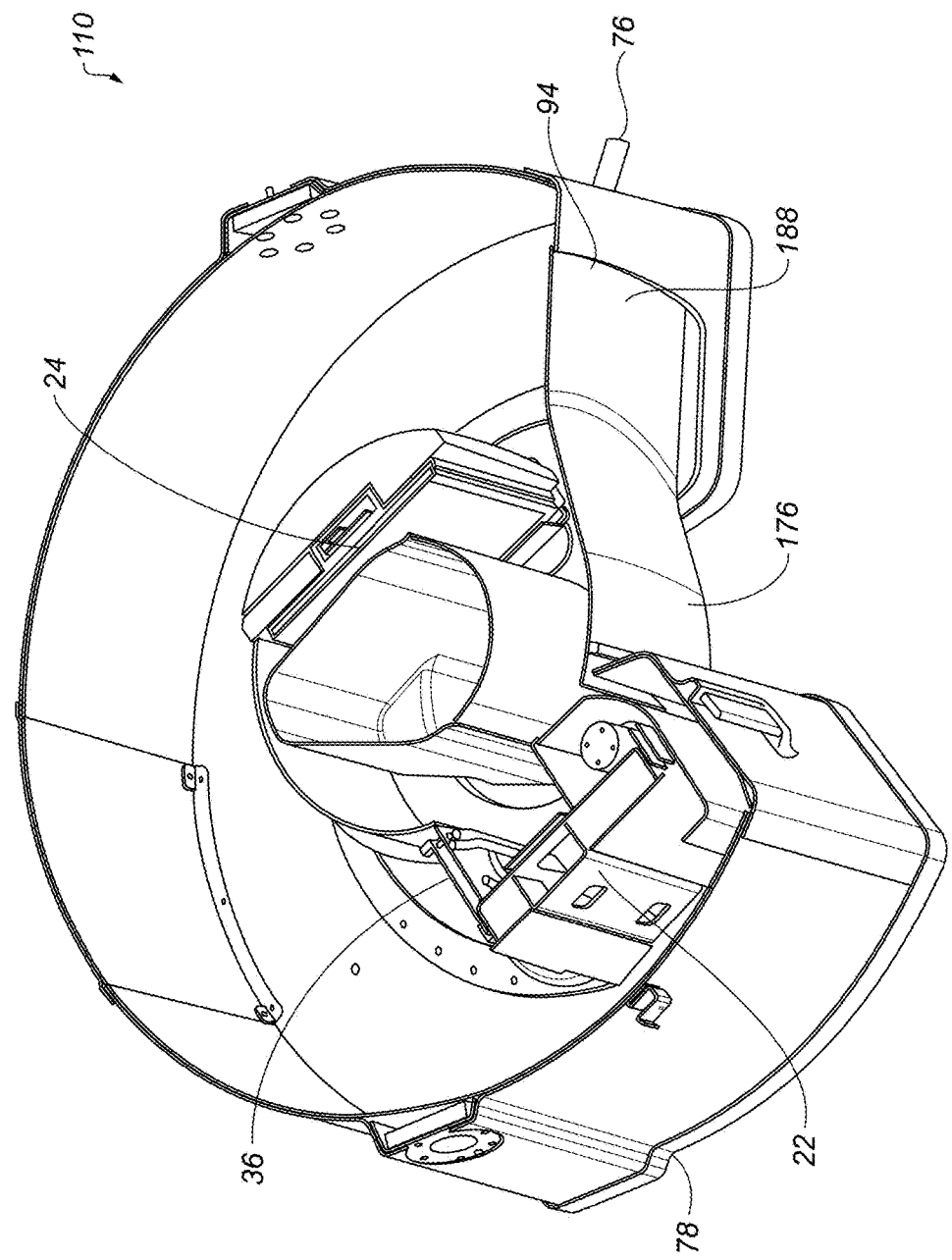
FIG. 21 is a perspective view of the scanner with the housing covers removed, showing the door in closed position.

The perspective view of FIG. 21, with the cover of housing 78 removed for visibility of internal parts, shows another feature of door 176. A closure portion 188 is provided as a part of door 176 to cover the gap that would otherwise be exposed when the door was closed. This covering keeps out dirt and debris and helps to prevent patient contact with, and visibility of, internal moving parts of scanner 110. According to an alternate embodiment, an edge 94 of closure portion 188 is attached to housing 78 and closure portion 188 folds or bends into place as door 176 pivots toward its closed position.

Radiographic imaging systems typically use a linear grid as an antiscatter device that improves contrast and signal to noise (S/N) ratio in radiographic images. A grid typically includes a series of lead foil strips that block x-rays separated by spacers that are transmissive to x-rays. The spacing of the strips determines the grid frequency, and the height-to-distance between lead strips determines a grid ratio. These and other grid characteristics can vary depending on the radiation energy that is used for a particular image. Calibration of the detector takes grid characteristics into account, so that different calibration data are used for different grids.

Certain exemplary embodiments according to the application can provide grid access for replacement with a different grid or removal of the grid from the imaging path. Scanner 110 has features that allow straightforward grid access and removal and that provide for repeatable registration of the grid to the detector when the grid is restored to position. Conventional CBCT imaging systems do not allow access to built-in flat panel detectors, and in particular, do not allow access to built-in flat panel detectors without invalidating electrical certifications, which can require various re-certifications of the CBCT imaging system before subsequent use.

In one embodiment according to the application, when necessary to replace or remove the grid prior to imaging, the operator performs a series of preparatory steps:

(i) Place the imaging system in a suitable mode for grid replacement. This is done, for example, by an operator instruction entered at a command console. In response to this instruction, the system temporarily disables its imaging capability and moves the internal gantry into an appropriate position for grid access.

(ii) Access and remove the grid from its position against the detector. Removal can be done by hand, that is, manually. In one embodiment, tools are not needed.

(iii) Optionally seat an alternate grid into position.

(iv) Restore normal imaging system operating mode. A second operator instruction, for example, indicates completion of the grid removal process, causing gantry 36 to be moved back to its appropriate resting position, ready for imaging.

Figure 22A:
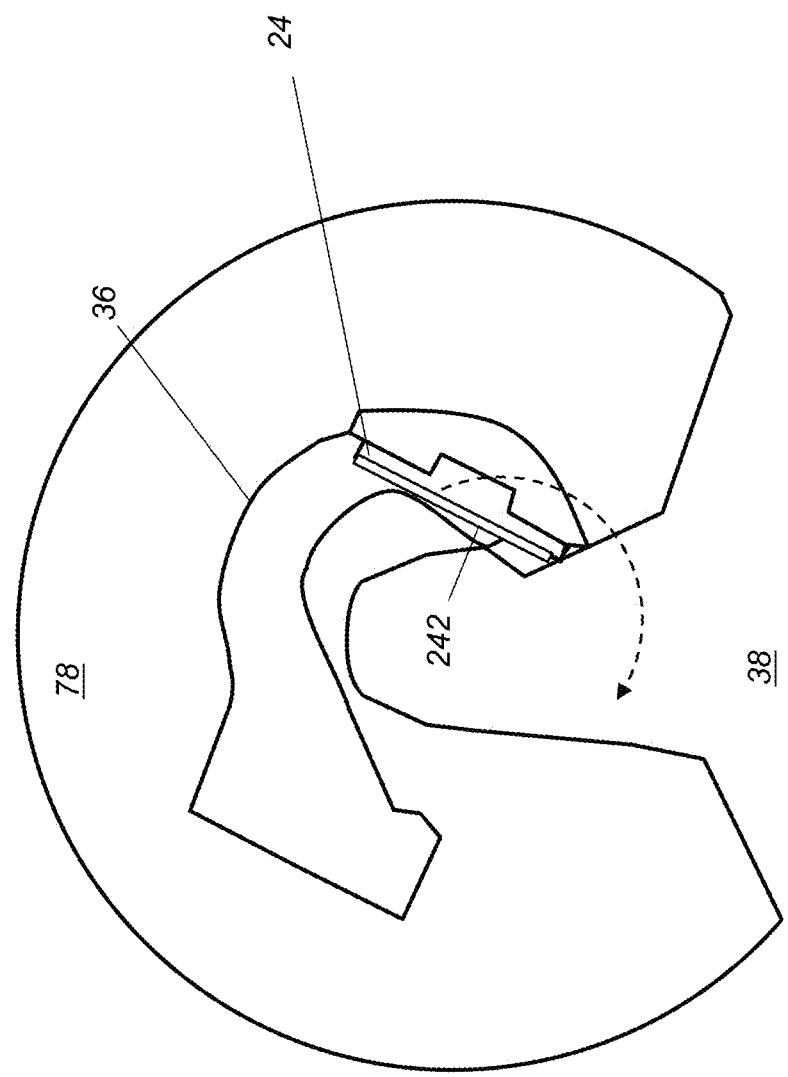
FIG. 22A is a top view of the imaging scanner with the gantry rotated to grid removal position.

FIG. 22A is a top view of the imaging scanner 110 with the gantry 36 rotated to a grid removal position within housing 78. Grid 242 is mounted against detector 24 and is accessible for removal in this position. The door (not shown in FIG. 22A for clarity) is pivoted to clear opening 38 for grid 242 removal. In one embodiment, removal can be through an opening that is provided in the door. Alternatively, removal of the grid 242 can be through an opening that is provided in the top or bottom surface of the scanner, or a sidewall of the gap 38.

Figure 22B:
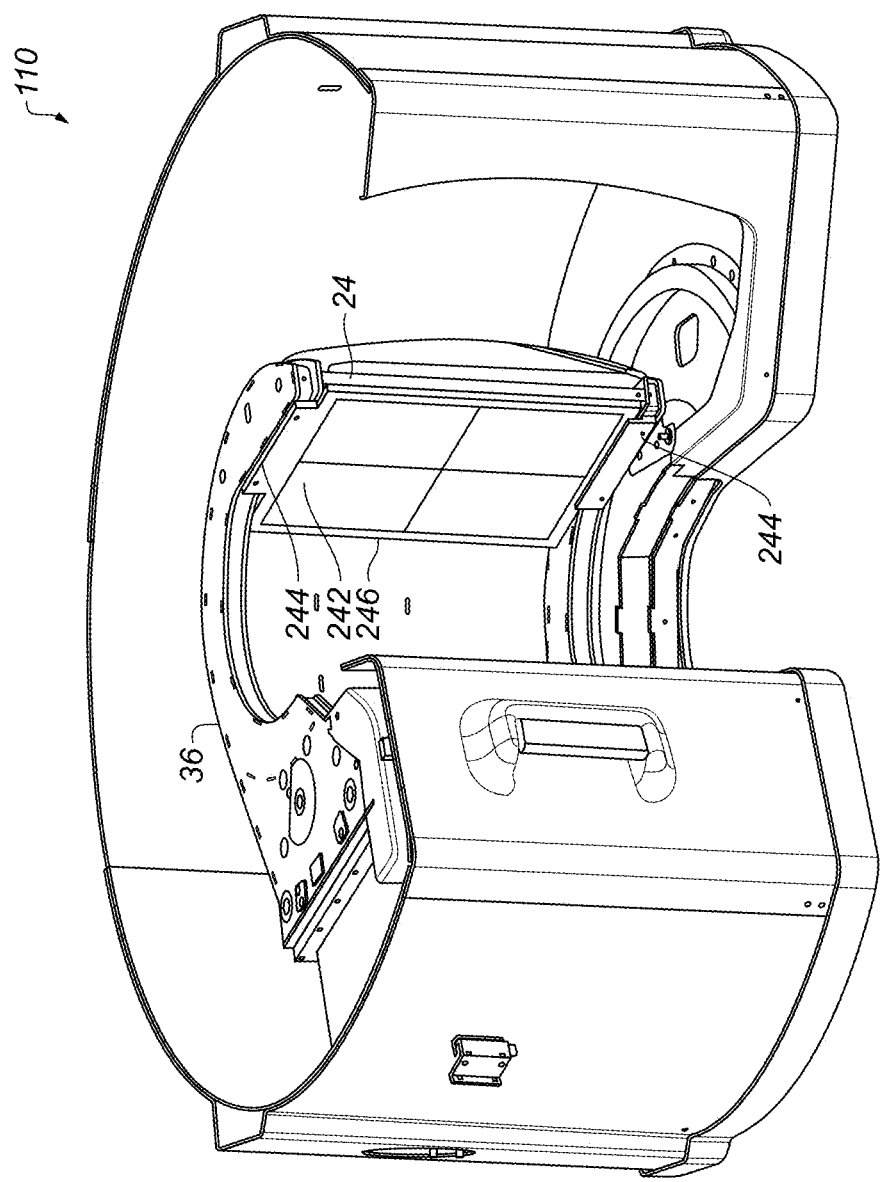
FIG. 22B is a perspective view of the imaging scanner with the gantry rotated to grid removal position.
Figure 22C:
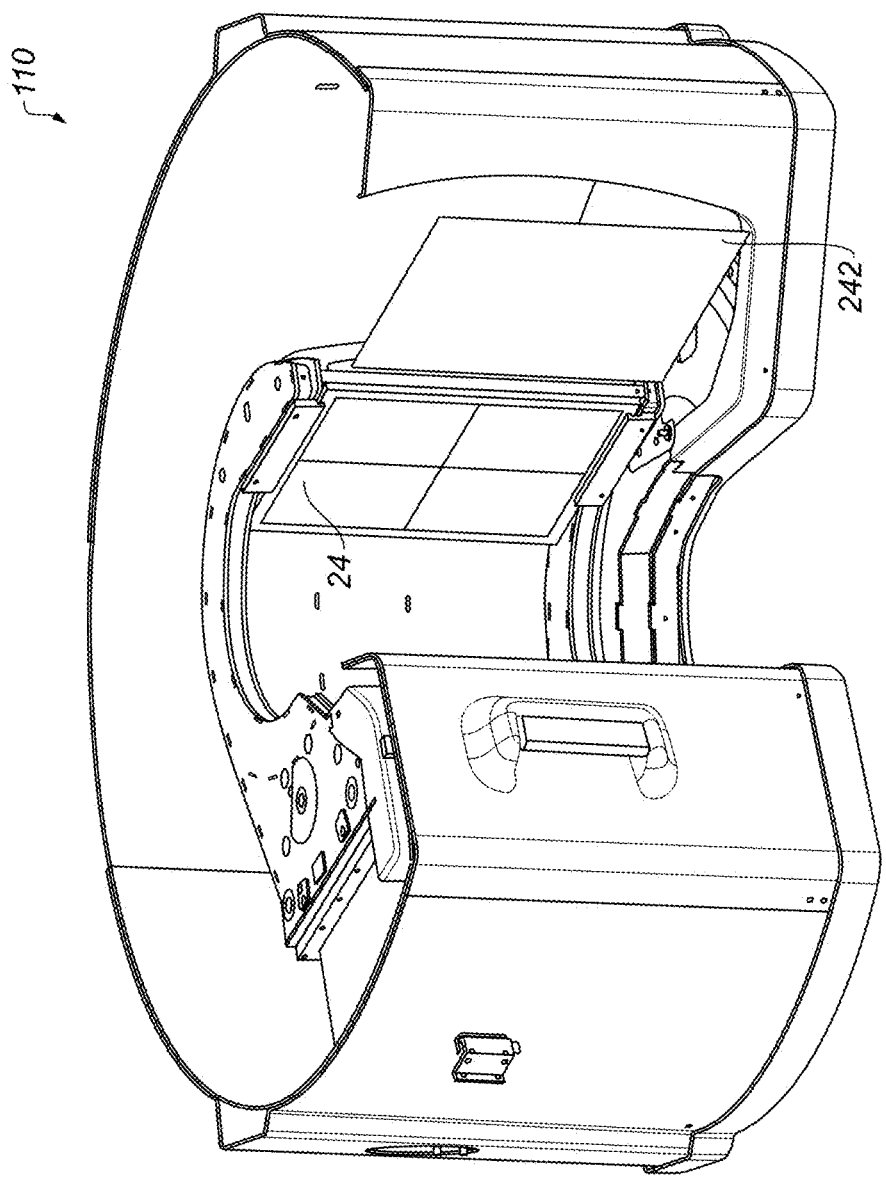
FIG. 22C is a perspective view of the imaging scanner with the gantry rotated to grid removal position and the grid being removed.

FIG. 22B is a perspective view of scanner 110 with gantry 36 rotated to its grid removal position, with the door and other internal components of scanner 110 removed for clarity. Brackets 244 and a stop 246 can seat grid 242 in position and registered against detector 24. According to an alternate embodiment, detents are provided so that grid 242 can be more precisely positioned. FIG. 22C shows grid 242 removed from its position.

According to one embodiment, a sensor (not shown) detects presence or absence of grid 242 and reports removal to an associated computer or dedicated processor that processes image data from detector 24. This causes different calibration tables or other data to be used, depending on whether or not grid 242 is in position and/or the type of installed grid.

In one embodiment in its position against detector 24 along the detector path, grid 242 is constrained for six degrees of freedom (DOF). This is provided by three-point constraint against detector 24, two-point constraint against stop 246, and a single point of constraint against bracket 244.

Exemplary embodiments herein can provide an imaging apparatus for cone beam computed tomography imaging of an extremity of a patient, the apparatus can include a support structure that includes a support column; a vertical translation element for positioning in a height direction to a height position along the support column; a rigid forked support arm that is configured to extend between a first end and a pair of extensions, where the first end of the rigid forked support arm is rotatably coupled to the vertical translation element, where the rotation of the first end of the rigid forked support arm is about an α axis that intersects the vertical translation element; and a scanner assembly that can include a scanner that comprises a radiation source energizable to direct radiation toward a detector during imaging operations of the imaging apparatus, and a scanner housing that encloses at least a portion of the scanner, where the radiation source and detector are configured to rotate at least 180 degrees with a prescribed spatial relationship within the scanner housing, where the scanner housing is rotatably coupled between the pair of extensions of the rigid forked support arm to rotate about a γ axis that is not parallel to the α axis.

In one embodiment, the α axis is substantially orthogonal to the γ axis. In another embodiment, the α axis is configured to intersect the γ axis. In one embodiment, the radiation source and detector are configured to rotate at least 180 degrees about a β axis that is substantially orthogonal to the γ axis, where the β axis passes through a scan volume of a scanner housing. In one embodiment, where the scanner housing can include a first surface; a second surface; an outer circumferential surface configured to connect the first and second surface; and an inner circumferential surface configured to connect the first and second surface to form a central opening extending from the first surface to the second surface, where the central opening surrounds a β axis that is orthogonal to the γ axis; where a peripheral gap is contiguous with the central opening to form an angular recess extending from the β axis to beyond the outer circumferential surface.

In one embodiment, a scanner housing defines a radially extending circumferential opening from an inner longitudinal axis to a radially outer circumferential surface of the housing, where the radially extending circumferential opening extends from a lower surface to an upper surface of the housing. In one embodiment, a door can be configured to reciprocally move between a first position and a second position, where in the first position the door is positioned to extend across and enclose a portion of the circumferential gap, and where in the second position the door is positioned to clear the portion of the circumferential gap, where the support column extends from a support base. In one embodiment, the door can include a closure portion that covers a gap in the scanner housing at least following door closing, wherein the door has a cylindrical surface facing the inner wall of the housing.

In one embodiment, a CBCT apparatus can further include an α axis rotational actuator that is energizable to rotate the forked support arm about the α axis; a γ axis rotational actuator that is energizable to rotate the scanner about the γ axis; and an operator control for at least the α axis rotational actuator, γ axis rotational actuator, and the vertical actuator. In one embodiment, a braking mechanism can stop motion of at least the vertical carriage translation element at power loss, where the vertical actuator comprises a ball screw mechanism or a pulley. One embodiment can include at least one remote operator control provided proximate to the scanner housing, the at least one remote operator control to control the vertical actuator, an α axis actuator to rotate the rigid forked support arm about the α axis, and a γ axis actuator to rotate the scanner about the γ axis.

In one embodiment, a CBCT apparatus can include a support structure; a scanner assembly coupled to the support structure, the scanner housing to enclose at least a portion of a scanner comprising a radiation source and detector configured to rotate at least 180 degrees with a prescribed spatial relationship within the scanner housing; a first device configured to move the scanner assembly along a vertical direction of the support column; a second device configured to revolve the scanner assembly to a vertical or other angular orientation; and a third device configured to orient the scanner assembly by revolving the scanner assembly about a different axis that the second device.

In one embodiment, a CBCT apparatus can include a graspable actuator, where a continuous motion of the graspable actuator in the α axis moves the scanner assembly continuously in the α axis direction, where a continuous motion of the graspable actuator in a horizontal direction moves the scanner assembly continuously in the γ axis direction, and where a continuous motion of the graspable actuator in the vertical axis moves the scanner assembly continuously in the vertical axis direction. In another embodiment, a CBCT apparatus can include a graspable actuator, where a first corresponding movement of the graspable actuator is configured to move the scanner assembly in the α axis direction, where a second corresponding movement of the graspable actuator is configured to move the scanner assembly in the γ axis direction, and where a third corresponding movement of the graspable actuator is configured to move the scanner assembly in the vertical axis direction.

In one embodiment, a method for acquiring cone beam computed tomography image data for an extremity can include a) providing a scanner apparatus that translates, at least partially about a scan volume, a radiation source along a source path and a detector along a detector path; b) responding to a first operator instruction by positioning the detector at a first predetermined position along the detector path for grid removal; and c) responding to a second operator instruction by positioning the detector at a second predetermined position along the detector path to initiate scanning of the scan volume. In one embodiment, the source and detector paths are within a housing that surrounds the scan volume, and where grid removal is through an opening in the housing, where the opening in the housing is within a peripheral opening of scanner apparatus configured to allow access to the scan volume, a top surface of the scanner apparatus or a bottom surface of the scanner apparatus. In one embodiment, the method can include d) modifying calibration data for the scanner apparatus according to removal of the grid; and e) acquiring image data from scanning the extremity.

Consistent with at least one embodiment, exemplary methods/apparatus can use a computer program with stored instructions that perform on image data that is accessed from an electronic memory. As can be appreciated by those skilled in the image processing arts, a computer program of an embodiment herein can be utilized by a suitable, general-purpose computer system, such as a personal computer or workstation. However, many other types of computer systems can be used to execute the computer program of described exemplary embodiments, including an arrangement of networked processors, for example.

The computer program for performing methods of certain exemplary embodiments described herein may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. Computer programs for performing exemplary methods of described embodiments may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that can be directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that computer program products for exemplary embodiments herein may make use of various image manipulation algorithms and processes that are well known. It will be further understood that exemplary computer program product embodiments herein may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the application, are not specifically shown or described herein and may be selected from such algorithms, systems, hardware, components and elements known in the art.

It should be noted that while the present description and examples are primarily directed to radiographic medical imaging of a human or other subject, embodiments of apparatus and methods of the present application can also be applied to other radiographic imaging applications. This includes applications such as non-destructive testing (NDT), for which radiographic images may be obtained and provided with different processing treatments in order to accentuate different features of the imaged subject.

Although sometimes described herein with respect to CBCT digital radiography systems, embodiments of the application are not intended to be so limited. For example, other DR imaging system such as dental DR imaging systems, mobile DR imaging systems or room-based DR imaging systems can utilize method and apparatus embodiments according to the application. As described herein, an exemplary flat panel DR detector/imager is capable of both single shot (radiographic) and continuous (fluoroscopic) image acquisition. Further, a fan beam CT DR imaging system can be used.

Exemplary DR detectors can be classified into the "direct conversion type" one for directly converting the radiation to an electronic signal and the "indirect conversion type" one for converting the radiation to fluorescence to convert the fluorescence to an electronic signal. An indirect conversion type radiographic detector generally includes a scintillator for receiving the radiation to generate fluorescence with the strength in accordance with the amount of the radiation.

Exemplary embodiments according to the application can include various features described herein (individually or in combination). Priority is claimed from commonly assigned, copending U.S. provisional patent application Ser. No. 61/710,832, filed Oct. 8, 2012, entitled "Extremity Scanner and Methods For Using The Same", in the name of John Yorkston et al., the disclosure of which is incorporated by reference.

While the invention has been illustrated with respect to one or more implementations, alterations and/or modifications can be made to the illustrated examples without departing from the spirit and scope of the appended claims. In addition, while a particular feature of the invention can have been disclosed with respect to one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An apparatus for cone beam computed tomography imaging of a subject, the apparatus comprising:
   an x-ray source;
   an x-ray detector;
   a removable antiscatter grid attached proximate to the detector;
   a rotatable gantry attached to the source, the detector, and the grid to rotate the source, the detector and the grid about an imaging axis; and
   a C-shaped housing enclosing the source, the detector, the grid, and the gantry, the C-shaped housing comprising an end wall at each one of two terminal ends of the C-shaped housing,
   wherein one of the end walls comprises an opening large enough to manually detach and remove the grid therethrough when the gantry is rotated to a grid removal position.

2. The apparatus of claim 1, further comprising a substantially vertical support column attached to the gantry and configured to controllably move the gantry vertically to a desired height position.

3. The apparatus of claim 2, further comprising a rigid dual-forked support arm attached to the support column and to the gantry, the dual-forked support arm configured to controllably rotate the gantry about an axis perpendicular to the vertical support column.

4. The apparatus of claim 3, further comprising a rotatable attachment assembly attached to the gantry and to the support arm, the rotatable attachment assembly configured to controllably rotate the gantry about an axis extending between two opposing ends of the dual-forked support arm.

5. The apparatus of claim 4, further comprising an operator control disposed proximate one of the two terminal ends of the C-shaped housing, the operator control comprising controls operable by an operator to controllably actuate the support column, the dual-forked support arm, the rotatable attachment assembly, or a combination thereof.

6. The apparatus of claim 5, further comprising an indicator to indicate an actuation of the support column, the dual-forked support arm, the rotatable attachment assembly, or a combination thereof.

7. The apparatus of claim 5, wherein the operator control is configured to move the gantry, rotate the gantry, or a combination thereof, for a preset distance when the operator control is actuated.

8. The apparatus of claim 1, wherein the gantry is configured to rotate the source and the detector at least 180 degrees about the imaging axis.

9. The apparatus of claim 1, wherein the detector is removable, and wherein the opening in said one of the end walls is large enough to remove the detector therethrough when the gantry is rotated to a detector removal position.

10. The apparatus of claim 1, further comprising a housing extension attached proximate to one of said end walls, the housing extension extensible from said one of said end walls to the other one of said end walls, wherein the housing extension is configured to enclose the source as the source rotates about the imaging axis.

11. An apparatus for cone beam computed tomography imaging of a subject, the apparatus comprising:
   a rotatable gantry;
   an x-ray source attached to the gantry;
   an x-ray detector attached to the gantry;
   a removable antiscatter grid attached proximate to the detector;
   a C-shaped housing enclosing the source, the detector, the grid, and the gantry, the C-shaped housing comprising an end wall at each one of two terminal ends of the C-shaped housing,
   wherein the gantry, the source and the detector are configured to rotate about an imaging axis, the source is configured to rotate along a source path, the detector is configured to rotate along a detector path, a length of the source path being longer than a length of the detector path, and
   wherein one of the end walls comprises an opening large enough to detach and remove the grid therethrough when the gantry is rotated to a grid removal position.

12. The apparatus of claim 11, wherein the opening is large enough to replace the removed grid by inserting and reattaching the removed grid or a replacement grid therethrough when the gantry is rotated to a grid replacement position.

13. A method of operating a cone beam computed tomography apparatus, the method comprising:
   attaching an x-ray source to a rotatable gantry;
   attaching an x-ray detector to the rotatable gantry;
   attaching an antiscatter grid proximate to the detector;
   enclosing the gantry, the source, the detector, and the grid within a C-shaped housing;
   providing an opening at one end of the C-shaped housing;
   actuating the gantry to rotate the grid proximate to the one end of the C-shaped housing; and
   manually detaching and removing the grid through the opening.

14. The method of claim 13, further comprising:
   actuating the gantry to rotate the detector proximate to the one end of the C-shaped housing; and
   manually detaching and removing the detector through the opening.

15. The method of claim 14, further comprising:
   actuating the gantry to rotate the gantry to a detector replacement position; and
   manually inserting and reattaching the removed detector or a replacement detector through the opening.

16. The method of claim 13, further comprising:
   actuating the gantry to rotate the detector proximate to the one end of the C-shaped housing; and
   manually inserting and reattaching the removed grid or a replacement grid through the opening.

* * * * *

UNITED STATES PATENT AND TRADEMARK OFFICE
CERTIFICATE OF CORRECTION

PATENT NO. : 10,034,641 B2
APPLICATION NO. : 15/656364
DATED : July 31, 2018
INVENTOR(S) : Michael A. Litzenberger et al.

Page 1 of 1

It is certified that error appears in the above-identified patent and that said Letters Patent is hereby corrected as shown below:

In the Specification

Column 14, Line 1    Replace "Further rotation about the a-axis" with --Further rotation about the α-axis--

Column 17, Line 10   Replace "volume is less than α second distance between the edges of" with --volume is less than a second distance between the edges of--

Signed and Sealed this
Twenty-third Day of July, 2019

Andrei Iancu
*Director of the United States Patent and Trademark Office*